United States Patent
Torris et al.

(10) Patent No.: US 8,945,065 B2
(45) Date of Patent: Feb. 3, 2015

(54) SYRINGE SAFETY ASSEMBLY

(75) Inventors: Anthony Torris, Montclair, NJ (US); Alistair Bramley, Brooklyn, NY (US); Dan Formosa, Piermont, NY (US); Eric Freitag, New York, NY (US)

(73) Assignee: UCB Pharma S.A., Brussels (BE)

( * ) Notice: Subject to any disclaimer, the term of this patent is extended or adjusted under 35 U.S.C. 154(b) by 20 days.

(21) Appl. No.: 13/532,382

(22) Filed: Jun. 25, 2012

(65) Prior Publication Data

US 2013/0079717 A1 Mar. 28, 2013

Related U.S. Application Data

(60) Provisional application No. 61/500,822, filed on Jun. 24, 2011.

(51) Int. Cl.
*A61M 5/00* (2006.01)
*A61M 5/32* (2006.01)
*A61M 5/315* (2006.01)

(52) U.S. Cl.
CPC ............. *A61M 5/3232* (2013.01); *A61M 5/326* (2013.01); *A61M 5/31573* (2013.01); *A61M 5/321* (2013.01); *A61M 2005/3264* (2013.01); *A61M 2207/00* (2013.01); *A61M 5/3204* (2013.01)
USPC ........................................... 604/187; 604/192

(58) Field of Classification Search
CPC ............ A61M 5/31573; A61M 5/321; A61M 5/3219; A61M 5/3232; A61M 5/326; A61M 2005/3264; A61M 2207/00
USPC .................. 604/110, 192, 197, 198, 116, 187
See application file for complete search history.

(56) References Cited

U.S. PATENT DOCUMENTS

| | | | | |
|---|---|---|---|---|
| 5,662,617 A * | 9/1997 | Odell et al. | | 604/192 |
| 6,558,353 B2 * | 5/2003 | Zohmann | | 604/158 |
| 6,869,418 B2 * | 3/2005 | Marano-Ford | | 604/192 |
| 8,277,437 B2 * | 10/2012 | Saal et al. | | 604/508 |
| 2007/0239117 A1 * | 10/2007 | Chelak et al. | | 604/198 |
| 2008/0171983 A1 * | 7/2008 | Knutson | | 604/117 |

FOREIGN PATENT DOCUMENTS

| WO | WO-2004043524 | 5/2004 |
|---|---|---|
| WO | WO-2009066130 | 5/2009 |

* cited by examiner

*Primary Examiner* — Theodore Stigell
(74) *Attorney, Agent, or Firm* — Ropes & Gray LLP

(57) ABSTRACT

Systems, devices, and methods are provided for providing safe syringe assemblies for injections. The syringe assemblies include a shielding mechanism that covers a syringe needle after an injection is delivered, thereby reducing the risk of a subsequent accidental stab from the needle. The shielding mechanism has a pre-injection configuration in which the needle extends beyond the housing and a post-injection configuration in which at least one component of the syringe assembly covers the needle. In some implementations, the syringe assembly includes a lock that inhibits the assembly from returning to the pre-injection configuration once an injection is delivered. The syringe assemblies may also include a bevel orientation mechanism that allows a user to align a needle bevel to accurately insert a needle for injection.

18 Claims, 25 Drawing Sheets

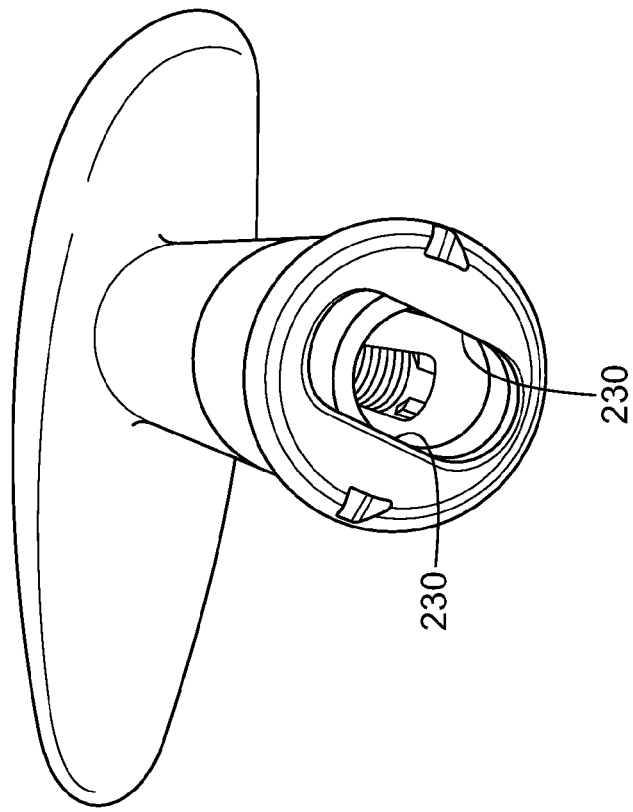
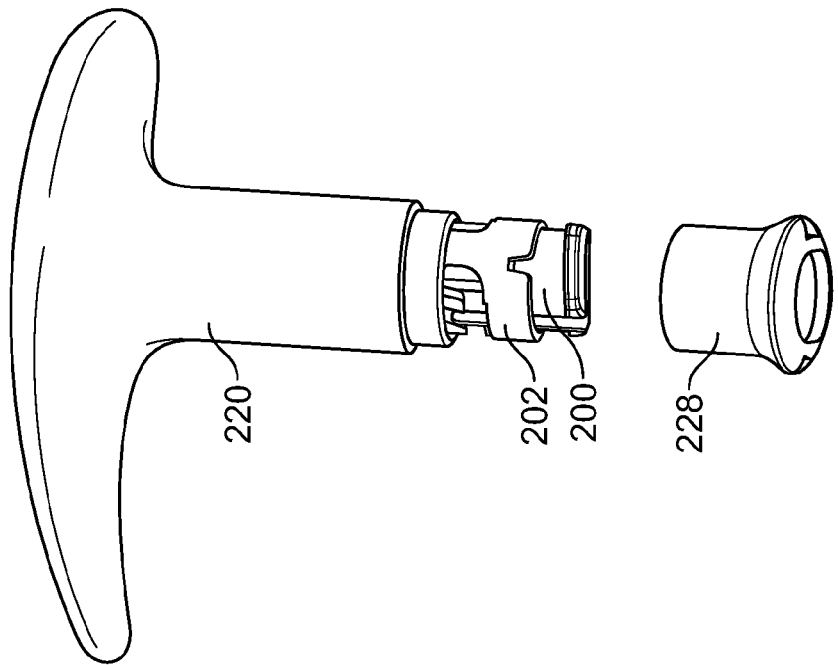
FIG. 21

US 8,945,065 B2

SYRINGE SAFETY ASSEMBLY

CROSS-REFERENCE TO RELATED APPLICATION

This application claims the benefit of U.S. Provisional Application No. 61/500,822, filed Jun. 24, 2011, which is hereby incorporated by reference herein in its entirety.

BACKGROUND

Many medical conditions require treatment that includes medication administered through injections or infusions. Injections are often administered on a regular schedule, and patients needing regular injections often inject the medication themselves. Patients may use conventional, single-use hypodermic syringes filled manually using medication ampoules for injections, or medication may be provided to a patient in single-use syringes that are pre-filled with a correct dosage of the medication. In both approaches, the syringes and needles used are disposed following a single injection for safety and health concerns.

Handling and disposal of syringes is a safety concern for both patients and medical professionals. Accidental stabs from handling syringes and needles are a common problem and can cause serious concerns for disease transmission. Typical syringes include a sheath on the needle that a user must remove prior to an injection and replace after the injection for disposal. Removal and replacement of the sheath requires a user to place his or her fingers in close proximity to an unshielded needle and can often lead to an accidental stab. In addition, a sheath is often attached to a syringe such that it will not fall off without a significant amount of force applied by a user, and the force required may lead to a slip and an accidental stab. After an injection is administered, a user handling a syringe may accidentally stab themselves while trying to re-shield or dispose of the used syringe and needle.

In addition to the risk of accidental stabs, conventional syringes may cause difficulties in inserting a needle at the correct location and minimizing the amount of pain caused by injections. Needles are provided with a bevel on the end of the needle that creates a sharp pointed tip to increase the ease with which the needle can be inserted into the skin. The sharp pointed bevel allows a user to accurately target an injection site and insert the needle in a way that reduces pain caused by the insertion. Typical syringes include a needle that is attached to the barrel of the syringe by a threaded attachment that does not allow the needle to rotate. To orient the bevel of the needle, a user may have to hold the syringe at an awkward angle and may have difficulty effectively controlling the syringe and needle.

Elderly patients and patients afflicted with rheumatoid arthritis may have difficulty safely handling and disposing of syringes and needles. The small size of needle covers and the force required to remove them can cause problems for patients who may be weaker or may not have a level of dexterity necessary to safely handle a syringe. In addition to creating an increased risk of accidental stabs from needles, a patient's age or medical condition may also make it more difficult to align a needle for an injection. Patients suffering from arthritis or other joint afflictions may find it painful or even impossible to orient the bevel of a syringe properly for an injection.

More effective syringe systems are needed to address these and other problems posed by currently available syringe systems. There is a need for a syringe system that shields syringe needles and protects a user after an injection is administered without requiring a user to carefully replace a small cap on the needle. There is also a need for syringe systems that facilitate orientation of the needle bevel of a syringe to give accurate injections and reduce patient pain.

SUMMARY

Described herein are systems, devices, and methods for providing a syringe assembly that automatically shields a needle of the syringe assembly after an injection is delivered. Also disclosed herein are systems, devices, and methods for providing a syringe assembly that allows a user to easily orient a needle and needle bevel prior to delivery of an injection.

Systems, methods, and devices for a syringe safety assembly are provided. An assembly contains a syringe for delivery of a medication dose via injection. A shielding mechanism is included that shields a syringe needle after an injection is delivered. A syringe assembly has an unshielded configuration in which a needle extends from the assembly and a shielded configuration in which a needle does not extend from the assembly. A transition from an unshielded configuration to a shielded configuration occurs when the syringe assembly is actuated during delivery of an injection. A locking mechanism locks the syringe assembly in the shielded configuration and prevents the needle from being re-exposed from the assembly.

Systems, methods, and devices for a syringe safety assembly are provided. An assembly contains a syringe for delivery of a medication dose via injection. A bevel orientation mechanism allows a user to fully rotate the syringe and orient the bevel of a syringe needle prior to injection. An assembly includes a bevel orientation collar that can be actuated and rotated by a user. The bevel orientation collar is coupled to a syringe within the assembly either directly or indirectly, and rotation of the bevel orientation collar rotates the syringe.

The systems, devices, and methods described herein provide syringe assemblies that allow a user to administer a more efficient and safe injection. In certain implementations, the syringe assemblies accommodate a variety of different syringes, including standard hypodermic syringes that may be filled from medication ampoules by a user as well as pre-filled syringes that are provided with a set dosage of medication already loaded into the syringe. A syringe assembly may be provided with a syringe already included in the assembly, or may be provided as a shell into which a syringe can be placed by a user.

The syringe assemblies described herein include a shielding mechanism that shields a syringe needle after an injection is delivered to a patient. The shielding mechanism is triggered when a patient delivers an injection and deploys a shield that covers the needle as it is removed from the injection site. The mechanism may lock the assembly in the shielded configuration with the needle covered so that further pressure applied by a user does not re-expose the needle. With the needle shielded, the syringe assembly may be safely handled until the syringe and needle are carefully disposed. The entire assembly may also be disposable.

In certain embodiments, a syringe assembly includes a housing with one or more retaining clips and a retainer. The housing includes an inner chamber with an opening for receiving a syringe and an opening for allowing a needle of the syringe to extend beyond the housing. A syringe placed into the housing may be pre-filled with a set dosage of medication or may be empty and filled with medication by a user prior to injection. A sheath is positioned within the housing, along with a spring that biases the housing towards one opening of the housing and biases the sheath towards another opening of the housing. The syringe assembly may be in an unshielded configuration with a needle exposed or a shielded configuration with the needle guarded within the housing. Actuation of the syringe assembly, for example, by delivery of an injection, causes the retainer to move in a direction perpendicular to the biasing spring force and release the retaining clips. The components of the assembly move from an unshielded configuration to a shielded configuration upon release of the retaining clips. In certain embodiments, a syringe assembly includes a top cover coupled to the housing.

In certain embodiments, retaining clips of a syringe assembly are provided as static components. The retaining clips extend from a housing and do not move relative to the housing during activation of the syringe assembly or during movement of components from an unshielded configuration to a shielded configuration. The movement from an unshielded to a shielded configuration may occur during delivery of an injection, and may be caused by the depression of a plunger into the syringe assembly. The plunger interacts with internal components of the syringe assembly to trigger the transition, and exerts force on a retainer that causes the retainer to move perpendicular to a longitudinal axis of an inner chamber of a housing to release the shielding mechanism. In certain embodiments, the plunger does not contact the retainer directly but contacts an intermediate actuator, which contacts and exerts a force on the retainer to cause the retainer to move perpendicular to a longitudinal axis of an inner chamber of a housing.

In certain embodiments, a syringe assembly includes a locking mechanism that prevents a syringe assembly from returning to an unshielded configuration once it has transitioned to a shielded configuration. A sheath is positioned within the housing of a syringe assembly and includes a locking mechanism that locks the housing and sheath in the shielded position. The locking mechanism may include a shelf on the housing that contacts legs on the sheath. In some embodiments, a syringe assembly includes first and second sheaths held within a housing. A lockout mechanism may include legs on the first sheath that contact a shelf on the second sheath. The legs may be compliant to allow the shelf to pass the legs when the first sheath and second sheath move from an unshielded configuration to a shielded configuration, and may be rigid to prevent the shelf from moving back past the legs once the assembly is in the shielded configuration.

In certain embodiments, a syringe assembly includes an outer top at a first opening of a housing, with a sheath held within the housing by the outer top. The outer top may be configured to receive a syringe inserted into the syringe assembly, and may have an opening shaped to match a shape of a collar on an inserted syringe.

In certain embodiments, the spring of a syringe assembly is positioned at a top opening of a sheath of the assembly. The spring may contact an interior sheath of the assembly directly to exert a biasing force on the sheath. The spring may be positioned around an interior chamber of a syringe assembly housing, and may surround a portion of a syringe inserted into the syringe assembly.

The syringe assemblies described herein may include a mechanism that facilitates orientation of a needle bevel for an injection. In certain implementations, internal components of a syringe assembly and a syringe held by the syringe assembly are configured to rotate independent of the outer housing. A user-actuatable component provides an easy way for a user to turn the needle and orient the syringe within the syringe assembly and the bevel of the needle extending from the syringe assembly.

In certain embodiments, a syringe assembly with a bevel orientation mechanism includes a housing having an inner chamber with a first opening for receiving a syringe and a second opening to allow a needle of a syringe to extend beyond the housing. The assembly includes a collar coupled to the second opening of the housing. Rotation of the collar relative to the housing drives rotation of a syringe inserted into the syringe assembly. In certain implementations, the collar is an independent component that can be separated from the housing. A user rotates the collar, for example, in a 360 degree rotation, to orient a needle bevel for an injection. In some embodiments, the collar directly contacts a syringe held within the syringe assembly and causes the syringe to rotate when the collar is rotated. In some embodiments, a holding component is positioned within the collar to operatively couple the collar to a syringe inserted into the syringe assembly. In certain embodiments, a collar is releasably coupled to a pull cap that covers a needle of a syringe assembly.

In certain embodiments, a syringe assembly with a bevel orientation mechanism includes a first sheath positioned within a housing. The first sheath may be coupled to a collar attached to the housing. The first sheath may include clips that are configured to mate with pockets on the collar to operatively couple the first sheath and the collar. The dips may be configured to be releasable to allow the sheath to move along a longitudinal axis of the inner chamber of the housing.

In certain embodiments, a syringe assembly with a bevel orientation mechanism includes a first sheath and a second sheath operatively coupled to the first sheath. The second sheath is configured to receive a syringe inserted into the syringe assembly. The syringe assembly may also include an outer top coupled to the second sheath, and the outer top may be shaped to match a shape of a collar of an inserted syringe. The syringe assembly may also include an inner housing that holds the second sheath within the housing of the syringe assembly. The inner housing preferably does not rotate relative to the housing, but may allow the second sheath and outer top to rotate relative to the housing. The inner housing may have at least one cutout that holds the outer top and allows rotation of the outer top while the inner housing remains static. Rotation of the collar may cause rotation of the inner sheath, outer sheath, and a syringe inserted into the syringe assembly relative to the housing.

In certain embodiments, a syringe assembly includes a housing having an inner chamber with a first opening for receiving a syringe and a second opening to allow a needle of the syringe to extend beyond the housing, with a sheath positioned within the housing. A spring exerts a force biasing the housing in a direction towards the second opening of the housing and biasing the sheath in a direction towards the first opening of the housing. A locking mechanism resists the biasing force of the spring, and a plate rotates to release the locking mechanism upon actuation of the syringe assembly.

In certain embodiments, a syringe assembly includes an inner sheath having a first opening and an inner chamber for receiving a syringe, and an outer housing having a second opening to allow a needle of the syringe to extend beyond the housing. A spring exerts a force biasing the sheath in a direction towards the first opening and biasing the housing in a direction towards the second opening. A locking mechanism resists the biasing force of the spring, and an activating member moves in a direction towards the second opening to release the locking mechanism upon actuation of the syringe assembly.

BRIEF DESCRIPTION OF THE DRAWINGS

The foregoing and other objects and advantages will be appreciated more fully from the following further description thereof, with reference to the accompanying drawings. These depicted embodiments are to be understood as illustrative and not as limiting in any way:

FIGS. 17-23 show illustrative steps of an assembly process for a syringe assembly;

DETAILED DESCRIPTION

To provide an overall understanding of the systems, devices, and methods described herein, certain illustrative embodiments will now be described. For the purpose of clarity and illustration, the systems and methods will be described with respect to a shielding assembly for pre-filled syringe cartridges. It will be understood by one of ordinary skill in the art that the systems and methods described herein may be adapted and modified as is appropriate, and that the systems and methods described herein may be employed in other suitable applications, such as for other types of syringes or injectors, and that such other additions and modifications will not depart from the scope hereof.

Figure 1:
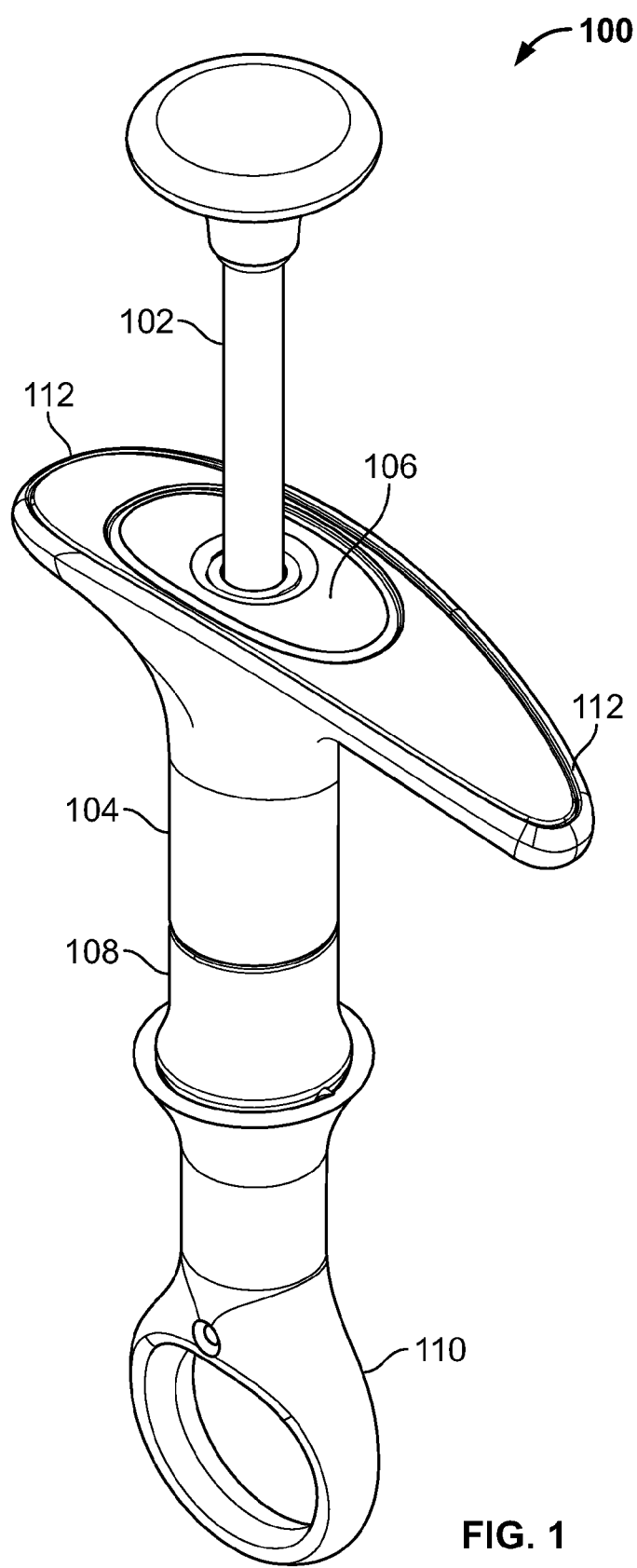
FIG. 1 shows a perspective view of an illustrative syringe assembly.
Figure 2:
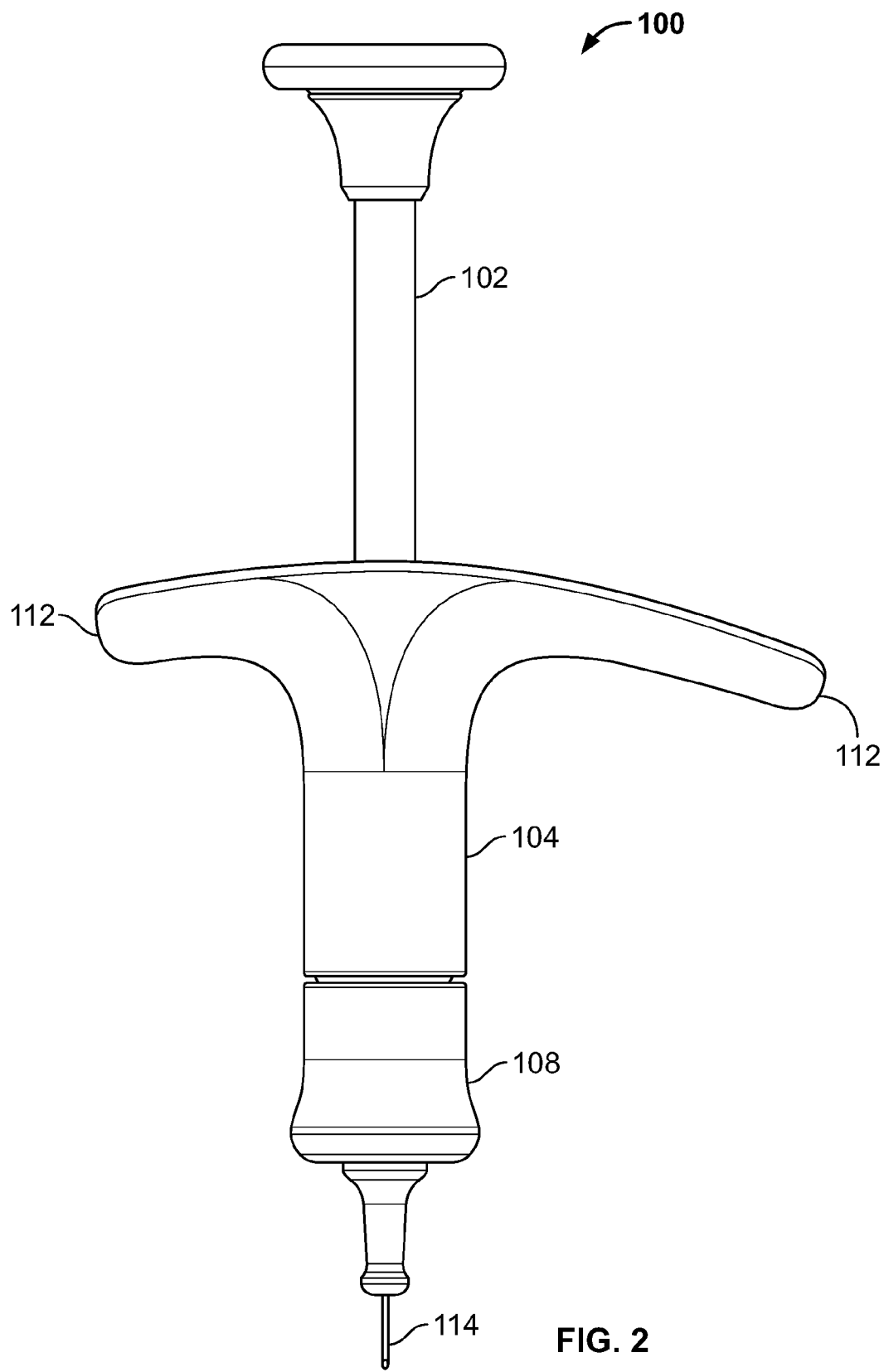
FIG. 2 shows a front view of an illustrative syringe assembly in an unshielded configuration.

FIGS. 1 and 2 show a syringe assembly 100 according to certain embodiments. The syringe assembly 100 includes a plunger 102, a housing 104 with a top cover 106, a bevel orientation collar 108, and a pull cap 110. The housing 104 has an inner chamber configured to receive a pre-filled syringe that contains a set dosage of a medication. To deliver an injection using the syringe assembly 100, a user can grab the handles 112 of the housing 104, remove the pull cap 110, turn the bevel orientation collar 108 to orient the bevel of the syringe needle 114, insert the needle 114 into an arm or any other location, and deliver the injection by depressing the plunger 102 down toward the housing 104.

The syringe assembly 100 is configured to allow a syringe to rotate freely within the housing 104. This full rotation allows the user to orient the bevel of the needle 114 in any desired orientation, which can increase the convenience of use and allow the user to deliver a more painless injection. To orient the bevel, a user rotates the bevel orientation collar 108 while holding on to the handles 112 of the syringe assembly 100. The bevel orientation collar 108 is coupled to the syringe contained within the housing 104, either directly or indirectly, via internal components of the syringe assembly 100. Rotation of the bevel orientation collar 108 causes the syringe held within the housing 104 to rotate and allows the user to orient the bevel in any desired orientation.

Figure 3:
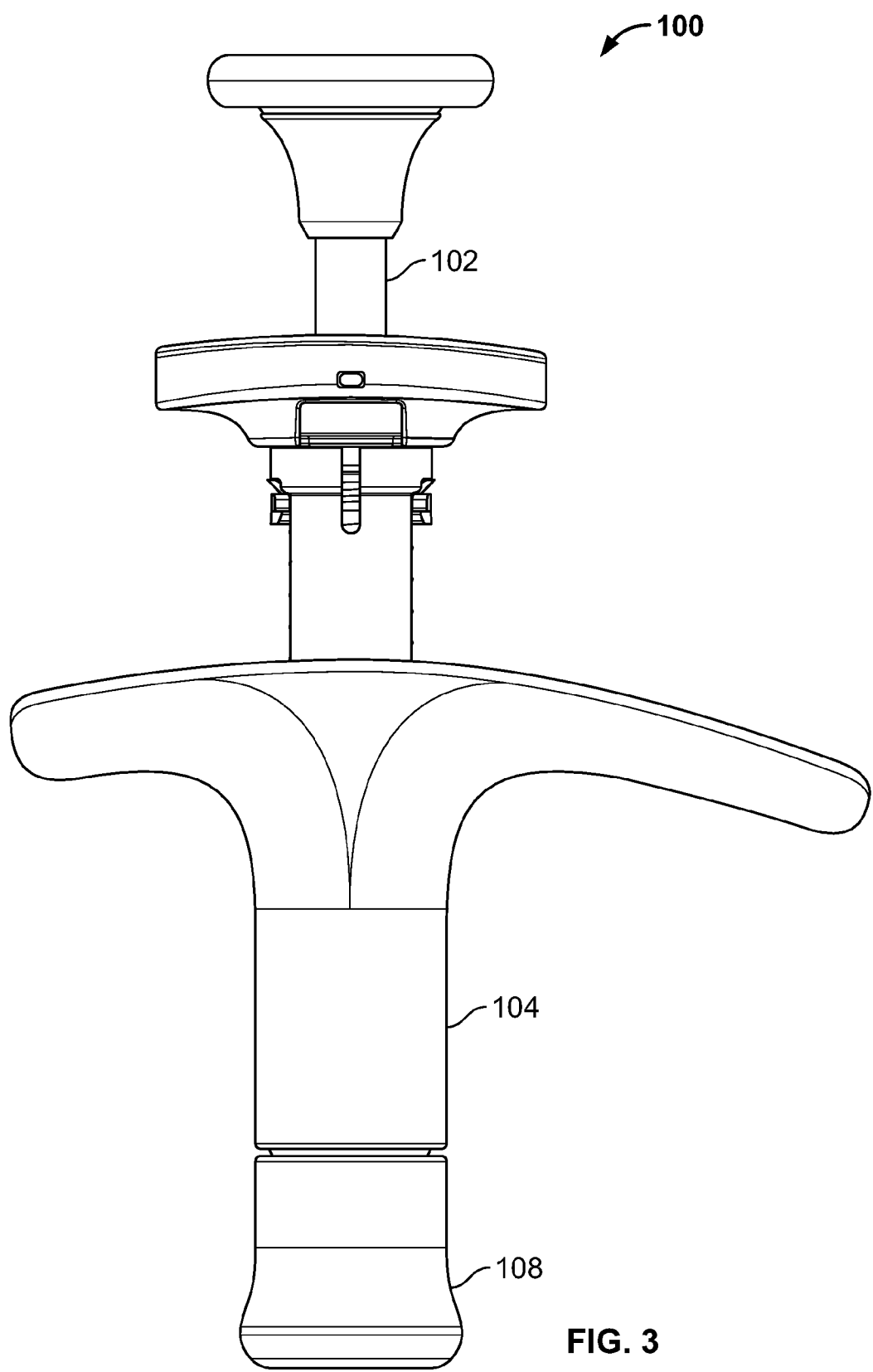
FIG. 3 shows a front view of an illustrative syringe assembly in a shielded configuration.

The syringe assembly 100 also contains a shielding mechanism that shields the needle 114 and protects the user after an injection is delivered. When the plunger 102 is fully depressed to deliver the injection, it activates the internal shielding mechanism of the syringe assembly 100. In certain embodiments, the shielding mechanism causes internal components of the housing 104 and a syringe held within the housing 104 to move upward, withdrawing the needle 114 into the housing 104. With the needle 114 withdrawn into the housing 104, the user is shielded from the needle 114 as shown in FIG. 3. The shielding mechanism may also include a lock that locks the syringe assembly 100 in the shielded configuration and prevents the needle 114 from being pushed back out of the housing 104. With the syringe assembly 100 in this shielded configuration, the syringe can be handled and disposed without risking a second stick of the needle 114 to the patient.

Figure 4:
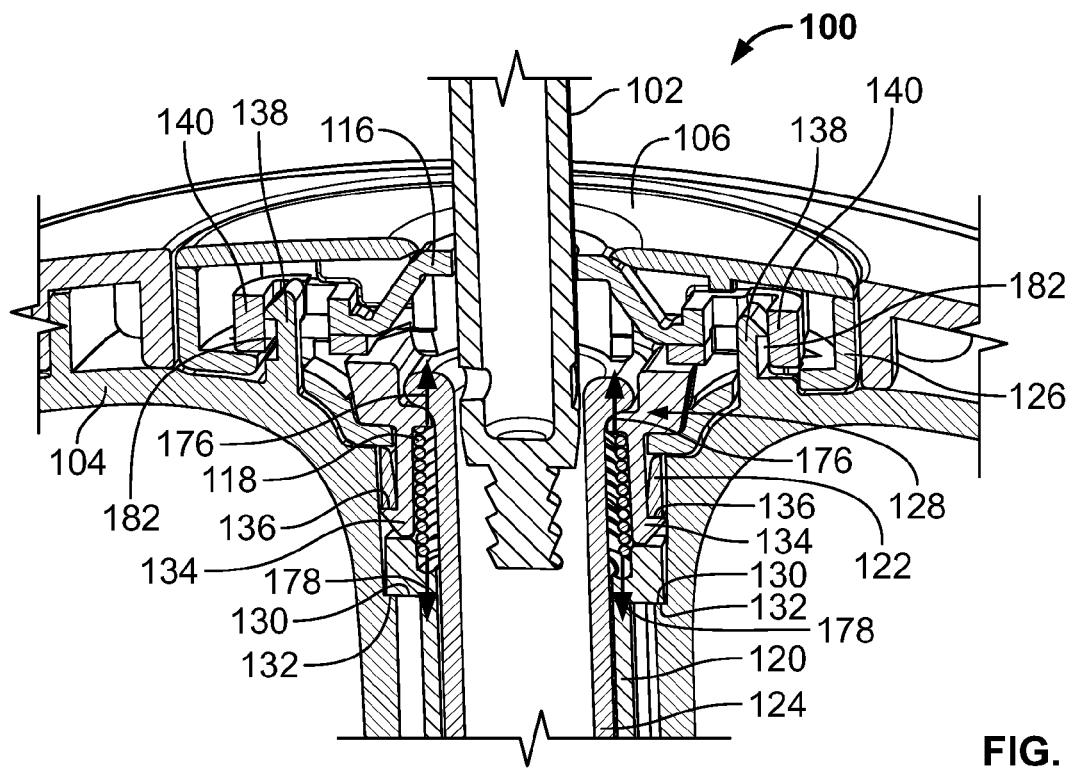
FIG. 4 shows a cross-section of an illustrative syringe assembly.

The transition from the unshielded configuration to the shielded configuration of the syringe assembly 100 begins when a user administers an injection. During the injection, the plunger 102 interacts with internal components of the syringe assembly 100 to unlock and trigger the needle shielding mechanism. FIG. 4 shows a cross-section of an upper portion of the syringe assembly 100 revealing internal triggering components that hold the syringe assembly 100 in the unshielded configuration. This view shows the housing 104, top cover 106, and plunger 102, as well as internal components that are part of the needle shielding mechanism. The interior components include a retainer 116, a spring 118, an inner sheath 120, an outer sheath 122, a syringe barrel 124, an inner housing 126, and an outer top 128. When the interior components are configured as shown in FIG. 4, the syringe is in the unshielded configuration, and the needle 114 at the lower end of the syringe barrel 124 is exposed from the housing 104 for an injection.

When the syringe assembly 100 is in the unshielded configuration shown in FIG. 4, the spring 118 is in a compressed state. The compressed spring 118 exerts a force on the outer top 128, biasing the outer top 128 upward in the direction of arrows 176, and exerts a force on the inner sheath 120, biasing the inner sheath 120 downward in the direction of arrows 178. Shoulders 130 on the upper end of the inner sheath 120 contact shoulders 132 on the housing 104 and prevent the force of the spring 118 from moving the inner sheath 120 downward. Clips 134 on the outer top 128 contact shoulders 136 on the outer sheath 122 and prevent the force of the spring 118 from moving the outer top 128 upward.

Figure 5:
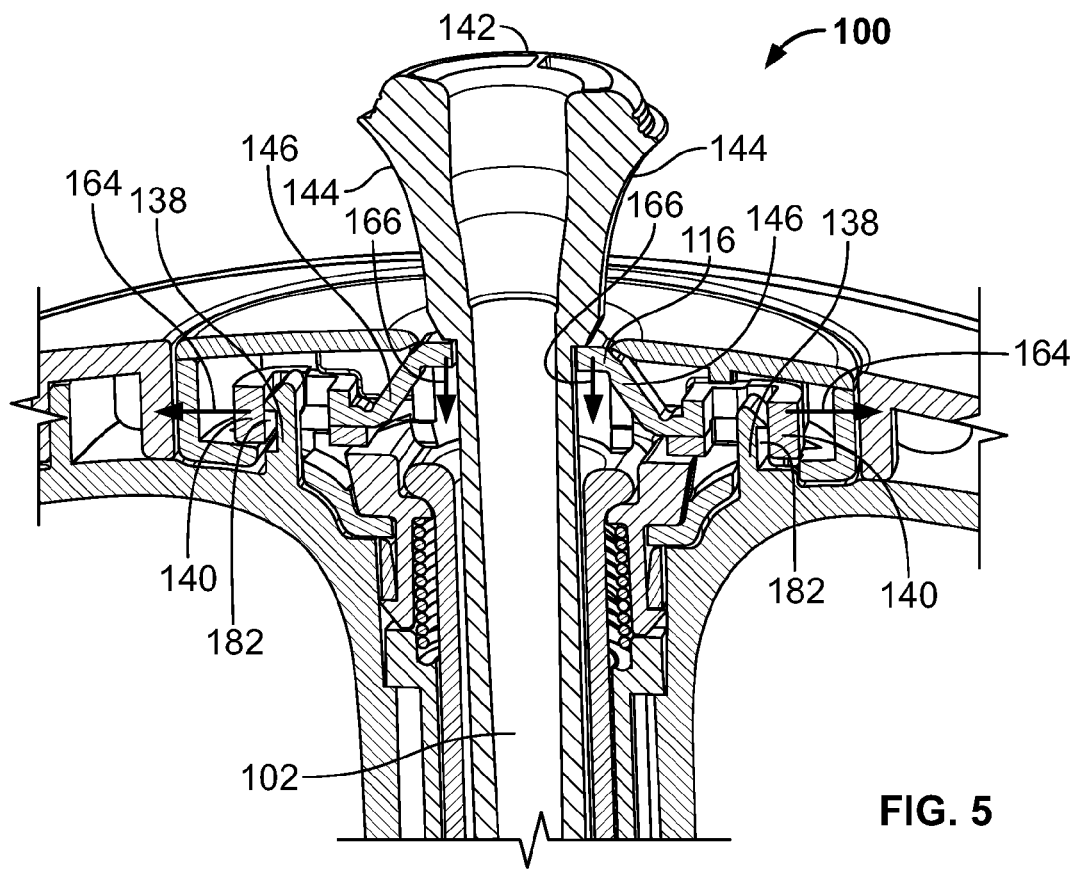
FIG. 5 shows a cross-section of an illustrative syringe assembly during delivery of an injection.
Figure 6:
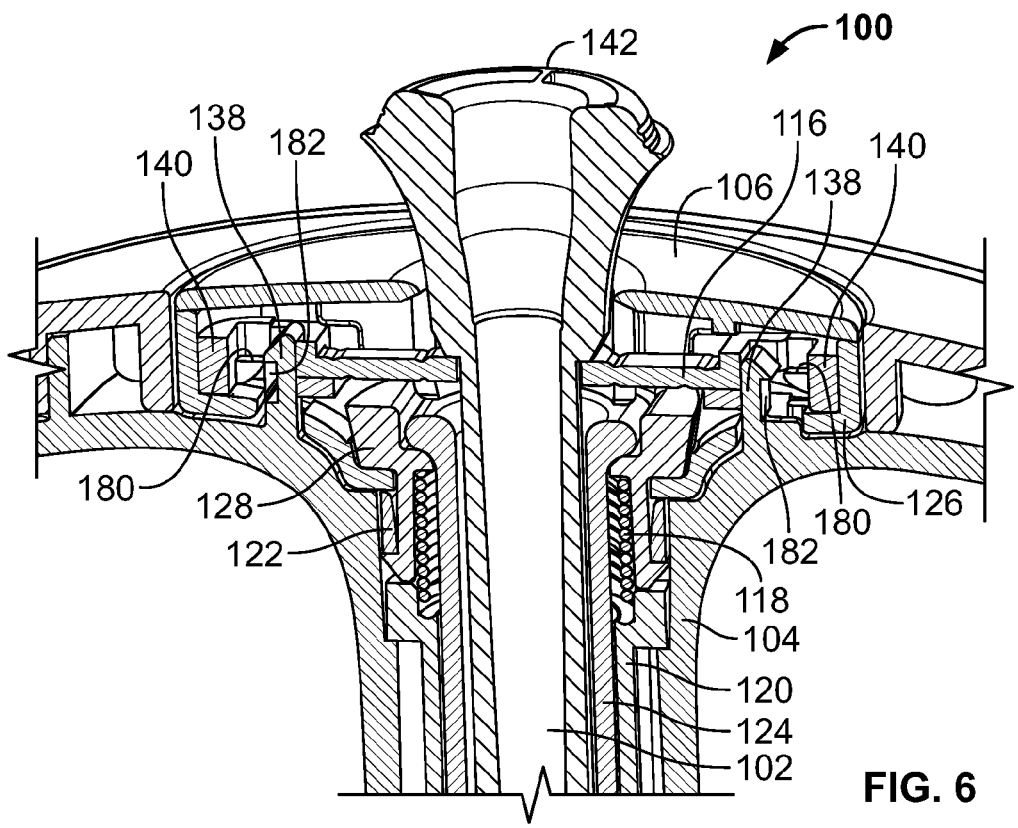
FIG. 6 shows a cross-section of an illustrative syringe assembly after an injection has been delivered.

The retainer 116 and retaining clips 138 hold the syringe assembly 100 in the unshielded configuration. In particular, the retaining clips 138 extend upward from an inner surface of the housing 104 and, as shown in FIGS. 4-6, latch on to the retainer 116 and resist the force of the spring 118. A platform section 180, shown in FIG. 6, on each of the lateral ends 140 of the retainer 116 fits under and interacts with an undercut portion 182 of each retaining clip 138. This interaction between the platform sections 180 on the retainer 116 and the undercut portions 182 on the retaining clips 138 prevents the spring 118 from forcing the inner sheath 120 and housing 104 downward and from forcing the outer sheath 122, inner housing 126, outer top 128, retainer 116 and top cover 106 upward. In certain embodiments, the retaining clips 138 are static and are not deflected by interaction with the retainer 116 or any other interior components of the syringe assembly 100. The retaining clips 138 may remain static and undeflected throughout delivery of an injection, triggering of the shielding mechanism, and movement of the assembly components during the transition from an unshielded configuration to a shielded configuration.

When the plunger 102 is depressed to deliver an injection, the downward driving motion of the plunger 102 releases the resistance provided by the interaction between the retainer 116 and the retaining clips 138, triggering the needle shielding mechanism. More particularly, as shown in FIG. 5, the head 142 of the plunger 102 has a curved undersurface 144 that contacts the retainer 116, indirectly or directly, and exerts a downward force on the retainer 116 in the direction of arrows 166. As the plunger 102 is depressed into the syringe barrel 124, bent portions 146 of the retainer straighten, thereby flattening retainer 116 and pushing the ends 140 of the retainer 116 laterally in the direction shown by arrows 164. The force exerted by the depressed plunger head 142 during injection thus causes the ends 140 of the retainer 116 to move laterally due to the geometry of the retainer 116, releasing the hold on the retaining clips 138 and allowing the inner syringe assembly components to spring into the shielded configuration.

An intermediate actuator, such as actuator 238 discussed below with respect to FIG. 23, may be used in the syringe assembly 100 to trigger the release of the retaining clips 138 when the plunger 102 is depressed. The actuator would interact with both the plunger 102 and a retaining member that holds onto the retaining clips 138. When the plunger 102 is depressed, it exerts a force on the actuator that is transferred to the retaining member and causes the retaining member to release the retaining clips 138. Depending on the inner configuration and geometry of a syringe assembly, an intermediate actuator may be preferred and may simplify the manufacturing process for the syringe assembly by allowing a retainer to be easily positioned to hold the retaining clips 138 before the actuator is inserted into the assembly and covered.

The release of retaining clips 138 by retainer 116 is shown in FIG. 6, which shows the retainer 116 and retaining clips 138 after the plunger 102 has been fully depressed, the retainer 116 has flattened, and the ends 140 of the retainer 116 have moved laterally. Once the retainer 116 and retaining clips 138 are in this configuration, there is no longer adequate resistance to overcome the forces of the spring 118. As a result, once the user releases pressure on the head 142 of the plunger 102, the spring 118 will extend, forcing the housing 104 and inner sheath 120 in a downward direction and forcing the top cover 106, retainer 116, inner housing 126, outer top 128 and outer sheath 122, along with the syringe barrel 124, in an upward direction.

The upward movement of the syringe barrel 124 caused by the force exerted by the spring 118 withdraws the needle 114 into the housing 104. When the spring 118 is fully extended, the syringe assembly 100 is in the completely shielded configuration shown in FIG. 7. In this configuration, the needle 114 is now covered by the housing 104, the inner sheath 120, and the bevel orientation collar 108. For safety, the user may not be able to push the needle 114 back out of the syringe assembly 100. This covering helps ensure that the user does not accidentally stab herself a second time after an injection is given. The shield also protects others, such as medical professionals, from accidental stabs and reduces the risk of disease transmission from the used needle 114.

Figure 8:
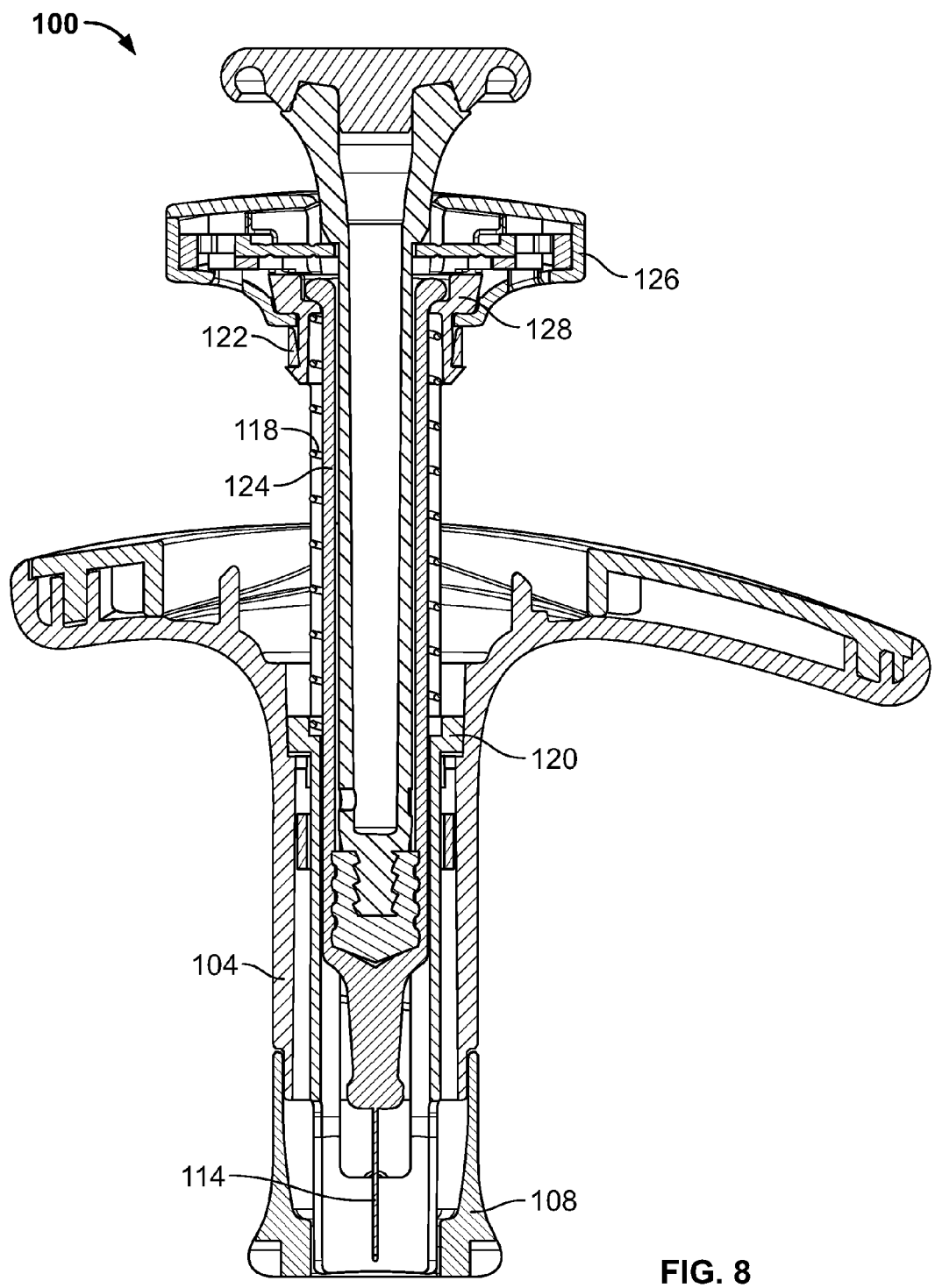

The relative movement of the exterior housing 104 of the syringe assembly 100 with respect to the internal components shields the needle 114. FIG. 8 shows a cross-section of the syringe assembly 100 in the shielded configuration. The outer sheath 122, outer top 128, and inner housing 126 have moved upward away from the housing 104 and the inner sheath 120, pulling with them the syringe barrel 124 and attached needle 114. In this configuration, the user is now protected from the shielded needle 114.

Figure 7:
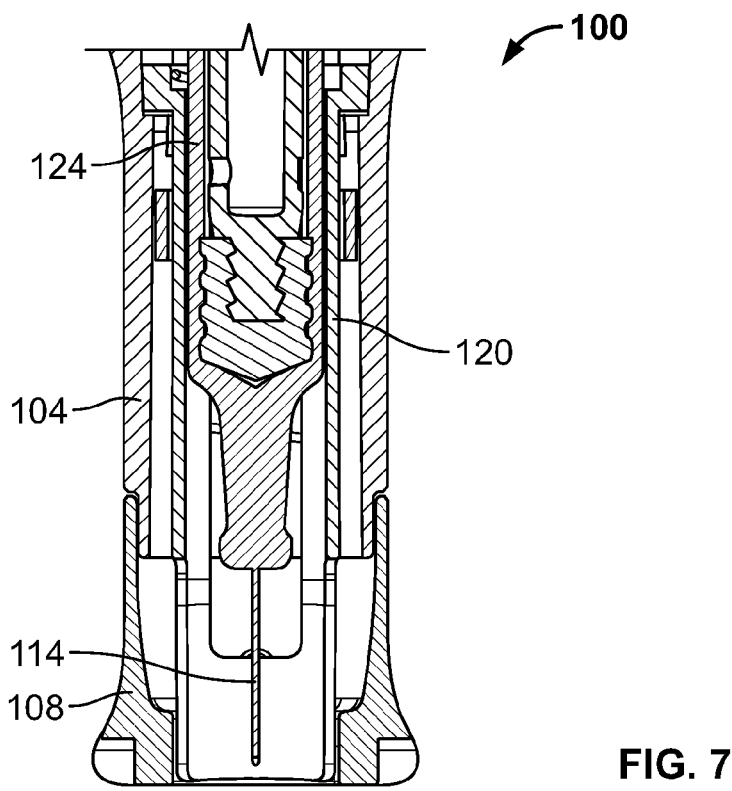
FIGS. 7 and 8 show a cross-sections of an illustrative syringe assembly in a shielded configuration.

Following an injection, a lockout mechanism of the syringe assembly 100 prevents the needle 114 from being re-exposed once the syringe assembly 100 is in the shielded configuration shown in FIGS. 7 and 8. In certain embodiments, the lockout may be caused by interaction between at least two of the components of the syringe assembly 100. For example, the lockout mechanism may be an interaction by the outer sheath 122 and the housing 104 or an interaction between the inner sheath 120 and the outer sheath 122.

Figure 9:
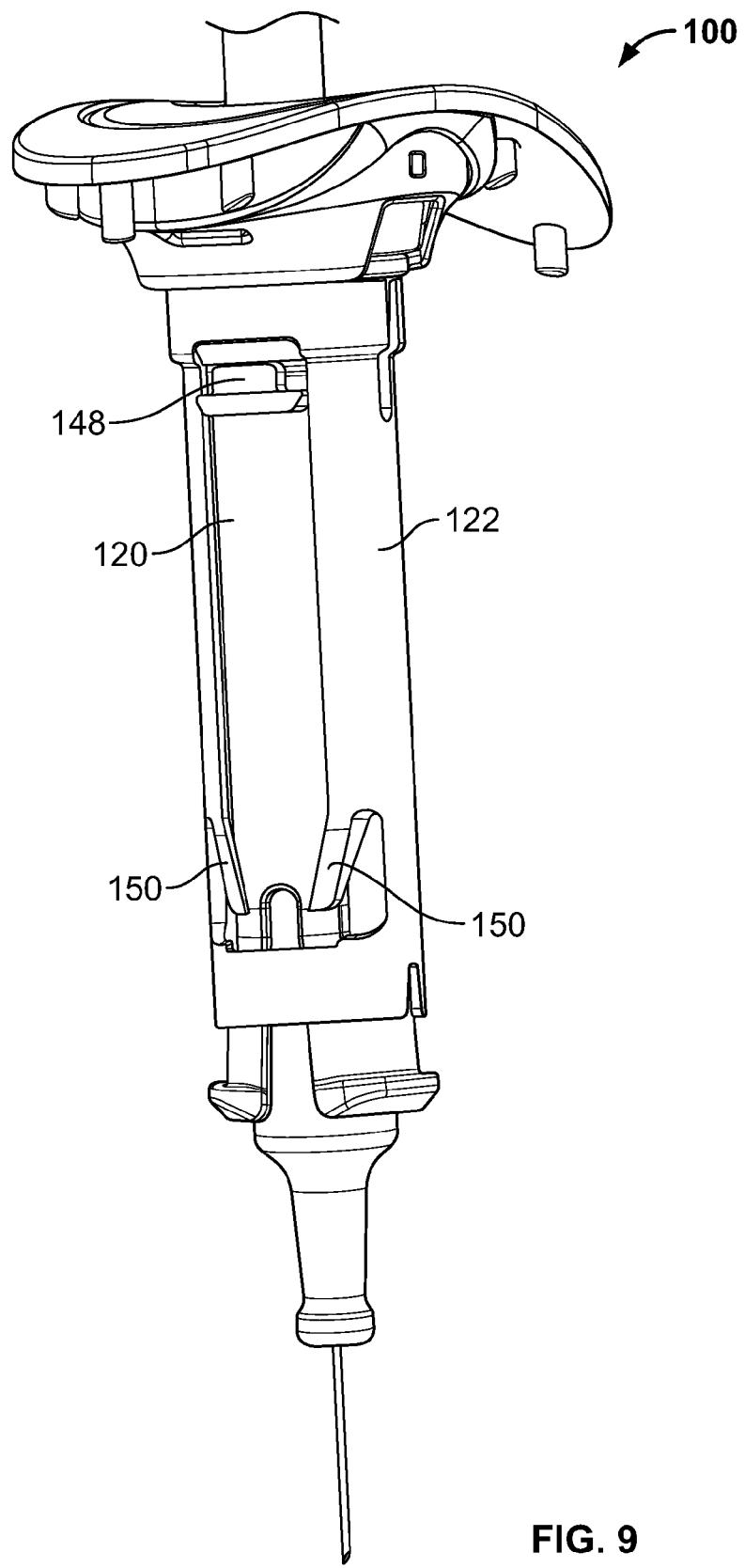
FIGS. 9-11 show internal lockout components of an illustrative syringe assembly.
Figure 10:
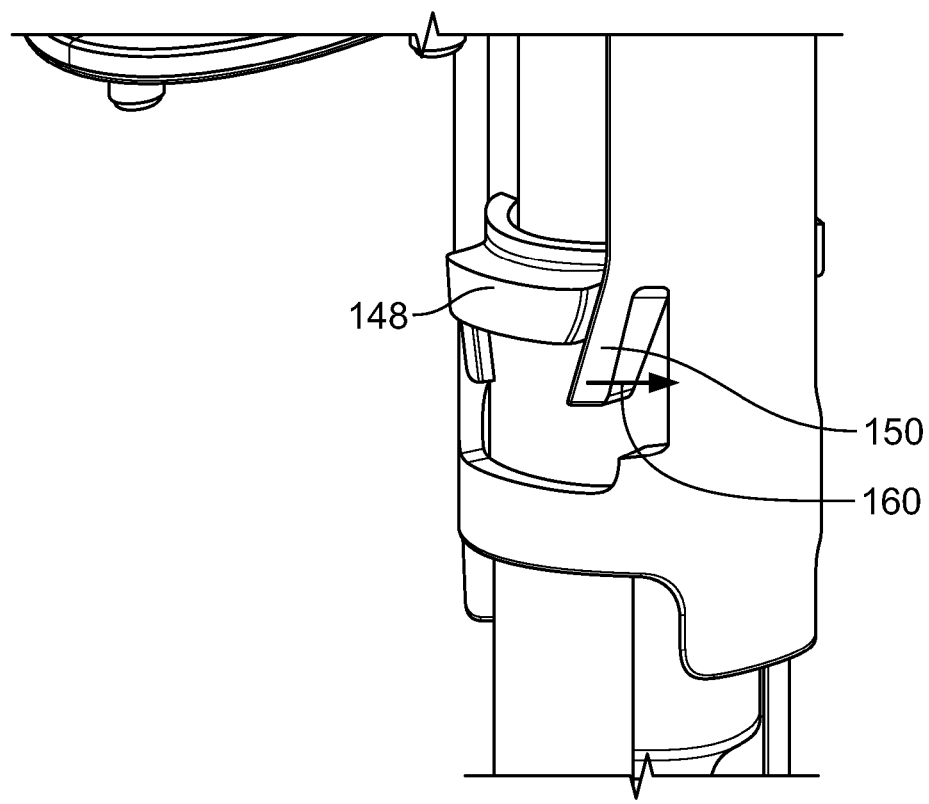

According to certain embodiments, the syringe assembly 100 is locked in the shielded configuration by an interaction between the inner sheath 120 and outer sheath 122 components as they move relative to each other when the spring 118 extends. FIG. 9 illustrates an example of a lockout mechanism of this type. As shown, the syringe assembly 100 is in the unshielded configuration, with the housing 104 removed. The lockout mechanism includes the shelf 148 of the inner sheath 120 and the legs 150 of the outer sheath 122. When an injection is delivered and the shielding mechanism is triggered, the force of the spring 118 causes the inner sheath 120 to move downward and the outer sheath 122 to move upward, thus causing the shelf 148 to move towards the legs 150. As the injection is delivered, the shelf 148 and legs 150 come into contact as shown in FIG. 10. The inner surfaces of the legs 150 contact the sloped outer surfaces of the shelf 148. In certain implementations, the legs 150 are made of a compliant plastic, such as a polyethylene material. Due to their geometry and the compliant material, the legs 150 of the outer sheath 122 deflect as the shelf 148 of the inner sheath 120 passes the legs 150. The deflection occurs, for example, in the direction of arrow 160.

Figure 11:
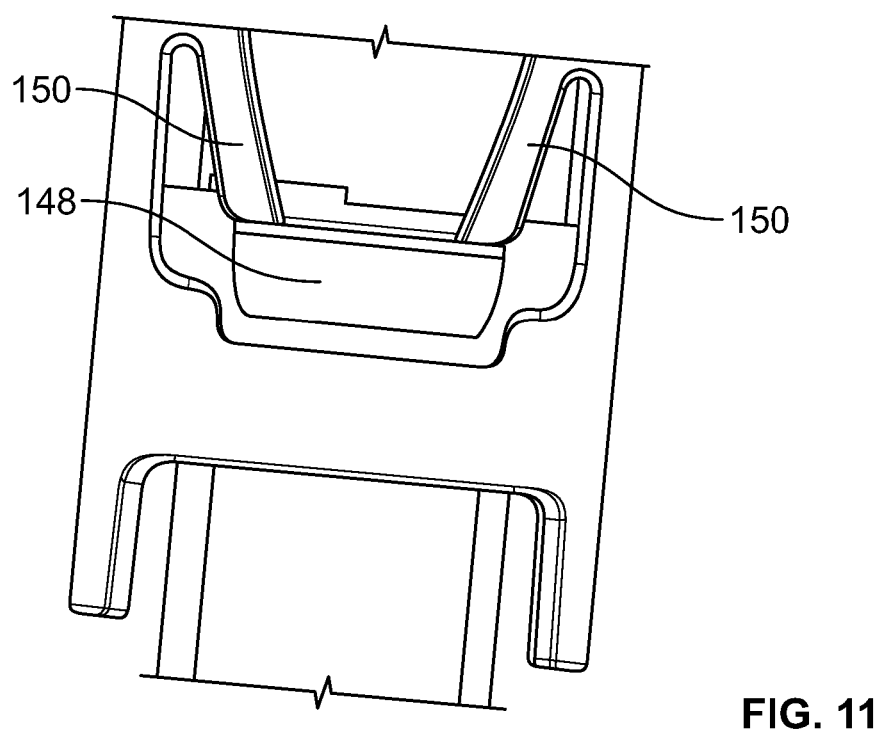

As shown in FIG. 11, after the shelf 148 passes the legs 150 as the spring 118 continues to extend, the legs 150 return to their original configuration, completing the lockout mechanism. In particular, the lower face of each leg 150 rests on top of the top surface of the shelf 148 after returning to their original configuration. The interaction between the legs 150 and the shelf 148 in the shielded configuration of the syringe assembly 100 prevents the shelf 148 from moving back towards the upper end of the syringe assembly 100 and therefore prevents movement of the outer sheath 122 downward past the shelf 148 and the inner sheath 120. Because the legs 150 are angled, they do not deflect further as would be needed for the legs 150 to pass back over the shelf 148. The interaction between the outer sheath 122, inner housing 126, outer top 128, and the upper end of the syringe barrel 124, shown in FIG. 4, pulls the needle 114 into the housing 104 as the legs 150 of the outer sheath 122 brace against the shelf 148 of the inner sheath 120 prevents the syringe from moving downward back through the inner sheath 120 and housing 104. With the components of the syringe assembly 100 locked in this configuration, the needle 114 is shielded from the patient and cannot be pushed back out beyond the housing 104 by further pressure on the plunger 102 applied by the user.

Figure 24:
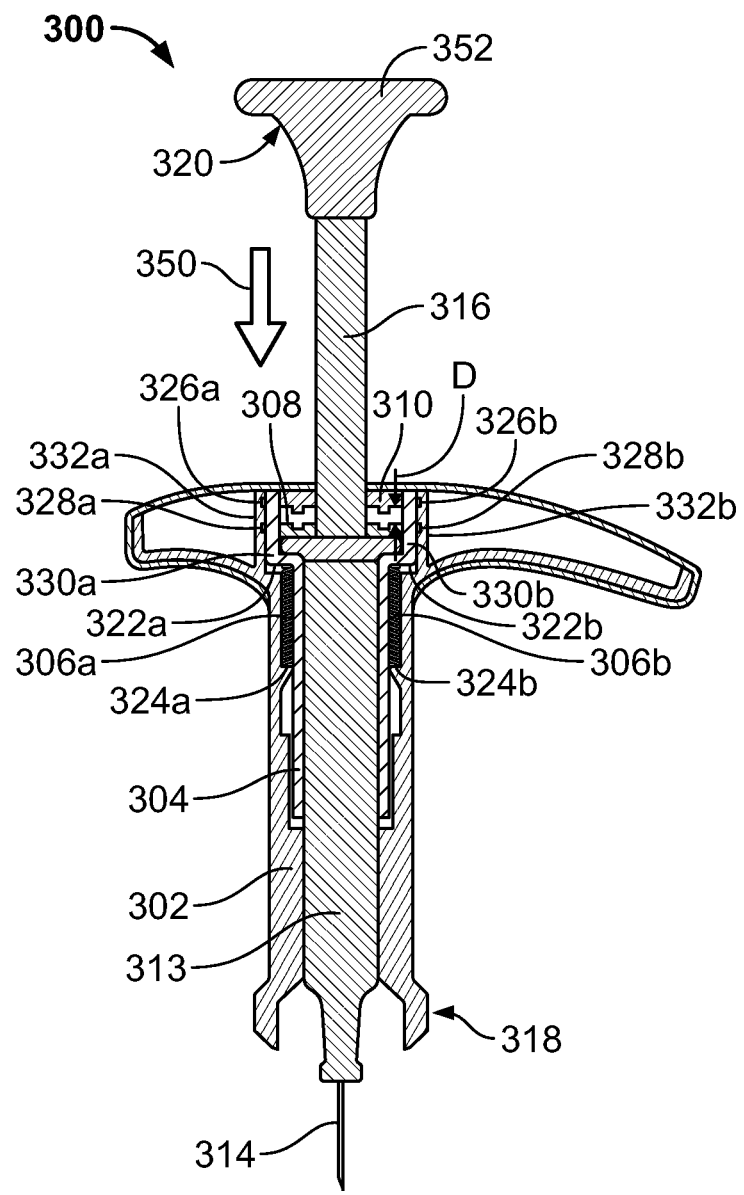
FIG. 24 shows an illustrative syringe assembly.

The needle shielding and locking mechanisms discussed above with respect to FIGS. 1-11 are merely illustrative, and alternative triggering and shielding mechanisms may be employed in some embodiments. For example, FIG. 24 shows an embodiment of a syringe assembly with a needle shielding mechanism that employs a triggering and shielding feature that differs from the syringe assemblies shown in FIGS. 1-11. In FIG. 24, a syringe assembly 300 is shown in a pre-injection configuration. An outer housing 302 holds a syringe 313 adapted to deliver an injection through needle 314. The syringe assembly 300 includes an inner housing 304 that is biased in a proximate direction from the outer housing 302 by two springs 306a and 306b. When an injection is delivered by depression of the plunger 316, an engaging plate 308 causes a rotating plate 308 to turn and triggers a shielding mechanism that retracts the syringe 313 and inner housing 304 proximately so that needle 314 is covered by a distal end 318 of the outer housing 302.

In the pre-injection configuration shown in FIG. 24, the springs 306a and 306h are compressed. The compressed springs exert a proximal force on the inner housing 304 and a distal force on the outer housing 302, thus biasing the two housings apart from each other. Spring 306a contacts the inner housing 304 at surface 322a, while spring 306b contacts the inner housing 304 at surface 322b. Likewise, the spring 306a contacts the outer housing 302 at surface 324a, and the spring 306b contacts the outer housing 302 at surface 324b. The contact between the springs and these surfaces produces the biasing force on the inner housing 304 and outer housing 302. The biasing forces from the springs are resisted in the pre-injection configuration by a locking mechanism on the engaging plate 308 and the rotating plate 308. The engaging plate 308 has two locking tabs 326a and 326b, while the rotating plate 308 has two locking tabs 328a and 328b. Before an injection is delivered, the locking tabs are disposed in a release slot that is disposed in walls 330a and 330b of the inner housing and walls 332a and 332b of the outer housing. The interaction between the locking tabs and the release slots, discussed below with respect to FIGS. 25 and 26, creates the triggering mechanism that releases the inner housing 304 and outer housing 302 to shield the needle 314 after an injection is delivered.

Figure 25:
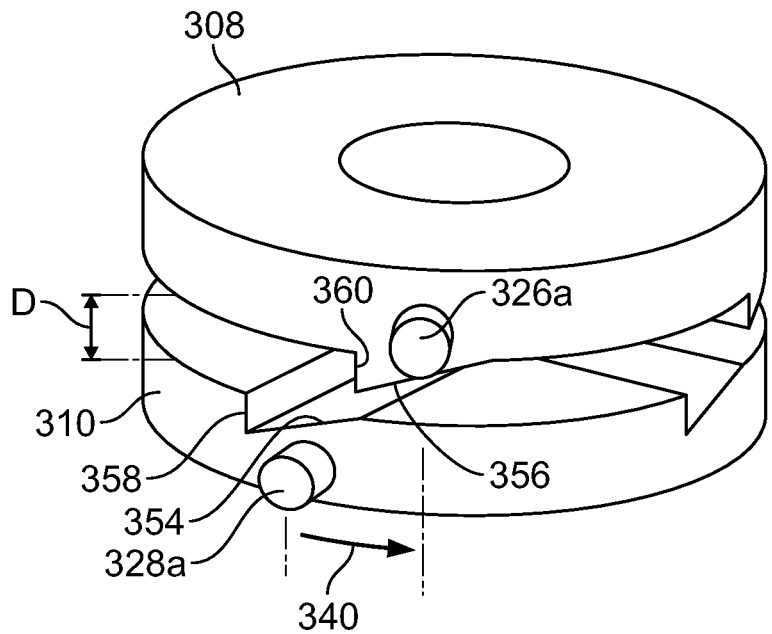
FIG. 25 shows engaging and rotating plates of the syringe assembly shown in FIG. 24.
Figure 26:
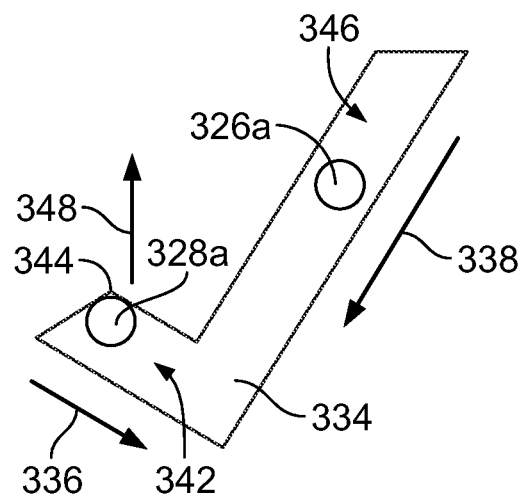
FIG. 26 shows a release slot of the syringe assembly shown in FIG. 25.

FIG. 25 shows the engaging plate 308 and the rotating plate 310 in the pre-injection configuration shown in FIG. 24. In this configuration, the two plates are separated by a distance D, and the locking tab 326a is offset from the locking tab 328a in the direction shown by arrow 340. The locking tabs 326a and 328a extend radially outward from the plates and into release slots in the inner housing 304 and outer housing 302. FIG. 26 shows the release slot 334 in which the locking tabs 326a and 328a are disposed.

As shown in FIG. 26, the offset between the locking tabs 326a and 328a is caused by the position of the locking tabs into two different arms 342 and 346 of the release slot 334. The arm 342 forms a corner 344 that contacts the locking tab 328a to resist the biasing forces of the springs 306a and 306b. The proximal biasing force of the springs pushes the inner housing 304 and the rotating plate 308 upwards in the direction of arrow 348 in FIG. 26, but the locking tab 328 contacts the corner 344 of the outer housing 302 and resists the proximal biasing force of the springs.

Figure 27:
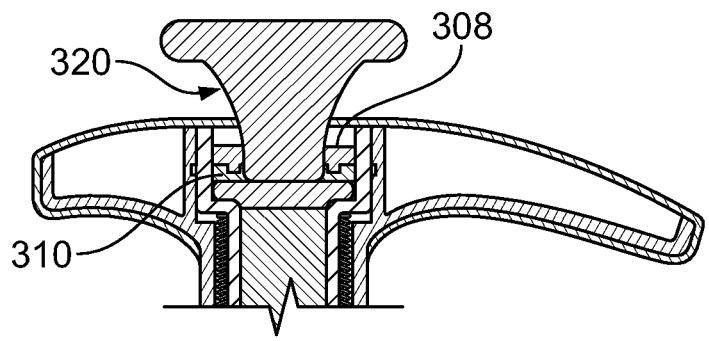
FIG. 27 shows a portion of the syringe assembly shown in FIG. 24 during an injection.
Figure 28:
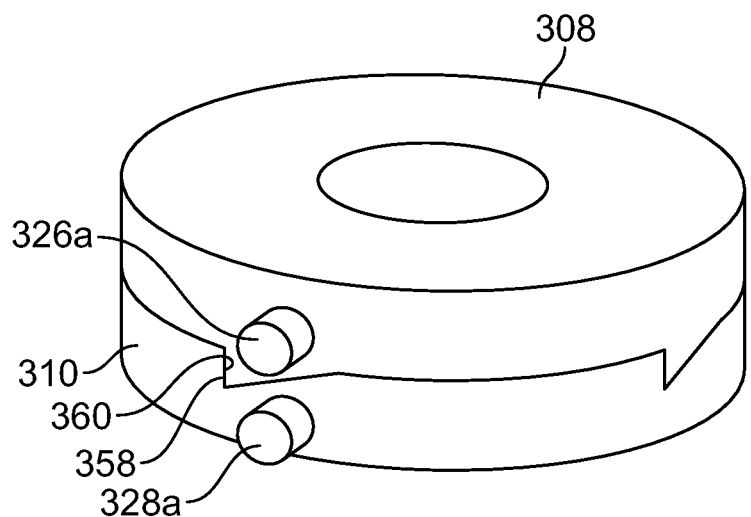
FIG. 28 shows the engaging and rotating plates shown in FIG. 25 during an injection.

From the pre-injection configuration shown in FIG. 24, an injection is delivered by depressing the plunger 316 in the distal direction shown by arrow 350. As the plunger is depressed, a lower surface 320 of the plunger head 352 enters the outer housing 302 and contacts the engaging plate 308, as shown in FIG. 27. The contact between the surface 320 and the engaging plate 308 pushes the engaging plate distally until it contacts the rotating plate 310. When the engaging plate 308 moves to close the distance D between the plates, a sloped surface 356 of the engaging plate 308 contacts a corresponding sloped surface 354 of the rotating plate 310. The distal force applied to the plunger head 352 in the direction of arrow 350 causes the rotating plate 310 to turn in the direction of arrow 340 shown in FIG. 25. The rotation is created by the interaction between the sloped surface 356 of the engaging plate 308 and the sloped surface 354 of the rotating plate 310. The rotating plate 310 continues to turn until a corner 358 contacts a corresponding corner 360 on the engaging plate 308. When the injection is delivered and the rotation is complete, the locking tabs 326a and 328A are aligned in the post-injection configuration shown in FIG. 28.

Figure 29:
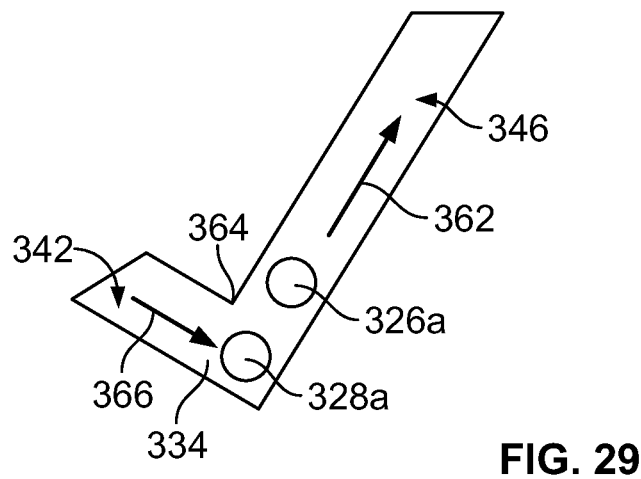
FIG. 29 shows the release slot shown in FIG. 26 during an injection.

In the post-injection configuration, the locking tabs 326a and 328a are aligned in the release slot 334 in the configuration shown in FIG. 29. In this configuration, the locking tab 328a of the rotating plate 310 has moved down arm 342 in the direction of arrow 366 and slightly past the corner 364 that connects the arms 342 and 346. From this position, the locking tab 328a is positioned to move up the second arm 346 in the direction of arrow 362 when the distal injection force is released from the plunger head 352. Thus, the force that delivers an injection from the syringe 313 also unlocks the shield locking mechanism of the syringe assembly 300.

Figure 30:
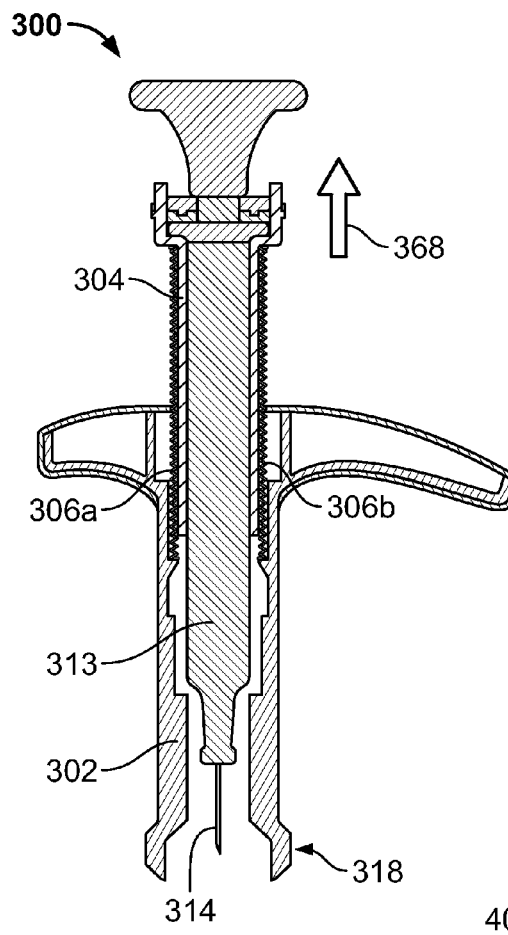
FIG. 30 shows the syringe assembly shown in FIG. 24 after an injection.

With the tab 328a positioned to move up the second arm 346 of the release slot 334, the contact between the tab 328a and the corner 344 that holds the springs 306a and 306b in their compressed state is released. As a result, after the injection, the two springs extend and separate the inner house 304 and outer housing 302, as shown in FIG. 30. In this shielded configuration, the delivery of the injection is complete and the springs 306a and 306b have fully extended. This extension pushes the inner housing 304 proximally out of the outer housing 302 in the direction shown by arrow 368. As a result, the needle 314 connected to the syringe is withdrawn into the outer housing 302. The lower end 318 of the outer housing 302 now shields the needle and decreases the risk of accidental stab from the needle 314. The assembly 300 may include a locking mechanism, such as the locking mechanism discussed above with respect to FIGS. 1-11, that locks the inner housing 304 and outer housing 302 in the shielded configuration and prevents the needle 314 from being pushed distally past the lower end 318 of the housing.

The syringe shields shown in FIGS. 1-30 employ a retraction shielding mechanism that withdraws a syringe proximately into a syringe housing when the mechanism is triggered. When the syringe is retracted proximately, the needle is withdrawn into the housing, which remains stationary and shields the needle after injection. In addition to these retraction shielding mechanisms, certain syringes may employ a forward shielding that extends a shield forward past the housing and over a needle rather than withdrawing the syringe and needle into the housing.

Figure 31:
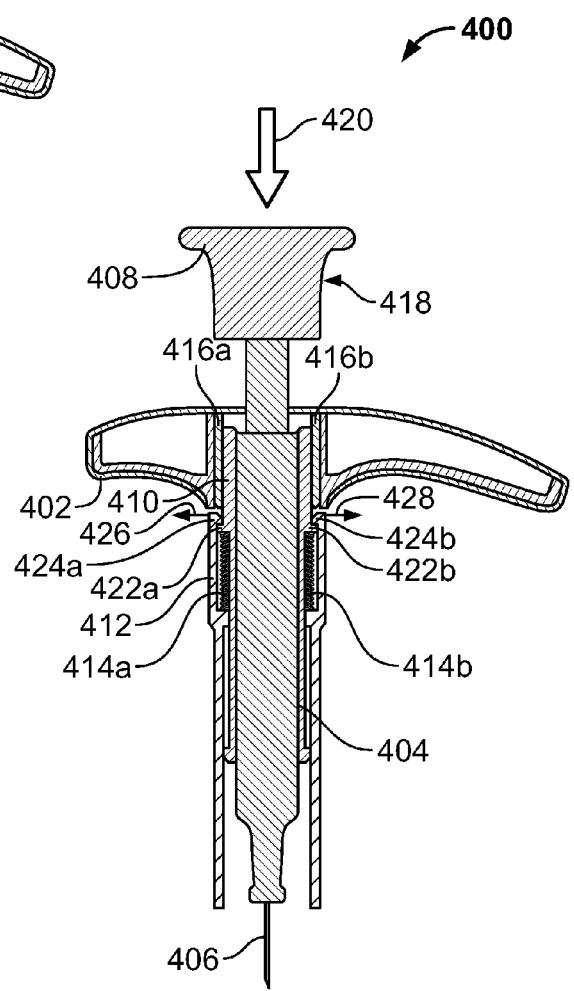
FIG. 31 shows an illustrative syringe assembly.

A forward shielding syringe assembly 400 is shown in FIG. 31. The assembly 400 includes a housing 402 that receives a syringe 404 adapted to deliver an injection. Within the housing 402 is an inner sheath 410 that interacts with an outer sheath 412 to form the mechanism that shields the needle 406 after the plunger 408 is depressed in the direction shown by arrow 420 to deliver an injection from the syringe 404. Two springs 414a and 414b bias the inner sheath 410 and outer sheath 412 in opposite directions. The compressed springs exert a proximal force on the inner sheath 410 that pushes the inner sheath towards the plunger 408 and exerts a distal force on the outer sheath 412 that biases the outer sheath toward the needle 406. To resist these biasing forces, platforms 422a and 422b of the inner sheath 410 contact clips 424a and 424b of the outer sheath 412. The contact between the platforms and clips resists the force exerted on the inner sheath 410 and the outer sheath 412 by the compressed springs 414a and 414b when the assembly 400 is in the pre-injection configuration shown in FIG. 31.

Figure 32:
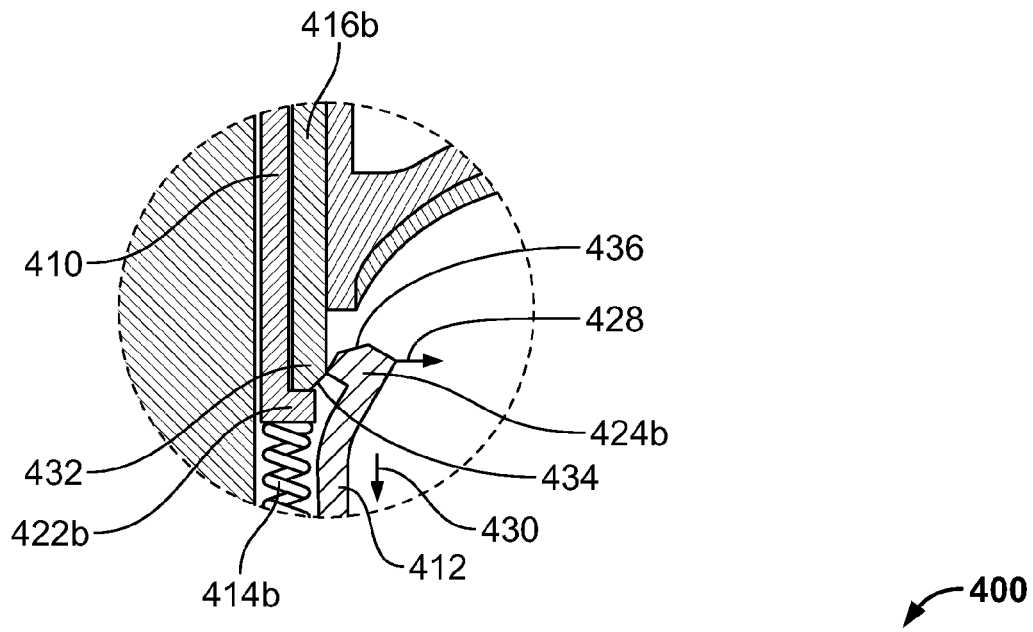
FIG. 32 shows a triggering mechanism of the syringe assembly shown in FIG. 31.

When an injection is delivered, the interaction between the platforms 422a and 422b and the clips 424a and 424b is interrupted by activating members 416a and 416b of the syringe assembly 400. When the plunger 408 is depressed to deliver an injection, a lower surface 418 of the plunger contacts the activating members 416a and 416b and transfers the distal force of the injection to the activating members. Each of the activating members 416a and 416b then contacts one of the clips 424a and 424b, respectively, and pushes the clips outwards in the directions shown by arrow 426 and 428. A close-up view of this activation is shown in FIG. 32. When the activating member 416b is pressed downward by the plunger 408, a tower end 432 of the activating member 416b contacts the clip 424b and causes the clip to move outward in the direction of arrow 428. A sloped surface 434 on the end 432 contacts a corresponding sloped surface 436 on the clip 424b such that the downward motion of the activating member 416b pushes the clip 424b outwards. When the clip is pushed outwards to the position shown in FIG. 32, there is no longer an interaction between the platform 422b and clip 424b to resist the biasing forces of the spring 414b. Thus, in this configuration, the outer sheath 412 is free to move distally in the direction of arrow 430 as the spring 414b extends.

Figure 33:
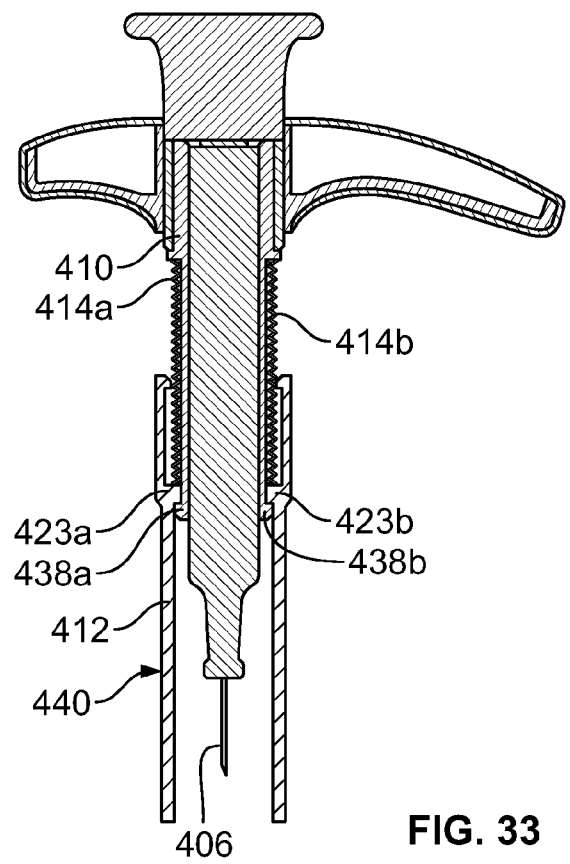
FIG. 33 shows the syringe assembly shown in FIG. 31 after an injection.

The distal movement of the outer sheath 412 shields the needle 406 in the post-injection configuration of the assembly 400, shown in FIG. 33. After the injection is delivered, the triggering mechanism is released, and the springs 414a and 414b extend. The outer sheath 412 is pushed distally until platforms 423a and 423b of the outer sheath contact distal clips 438a and 438b of the inner sheath 410. The contact between the platforms and the distal clips resists any further movement of the outer sheath 412. In this configuration, the needle 416 is covered by a distal end 440 of the outer sheath 412. In addition to the triggering and forward shielding mechanism of the assembly 400, the assembly may include a locking mechanism that locks the outer sheath 412 in the position shown in FIG. 33 and resists movement of the outer sheath back in the proximal direction. Such a locking mechanism reduces the risk of an accidental stab of needle 406 by preventing the needle from being pushed back out past the tower end 440 of the outer sheath 412 from the shielded configuration.

Figure 34:
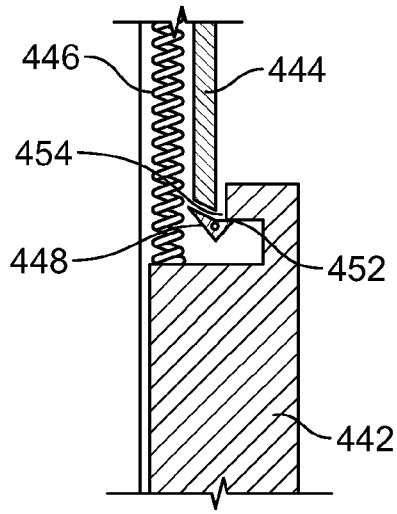
FIG. 34 shows an illustrative triggering mechanism.

In addition to the platform and clip interaction shown in assembly 400, other triggering mechanisms may be employed in a forward shielding syringe assembly. For example, FIG. 34 shows a triggering mechanism that uses an over center cam 448 and an activating member 444. In the pre-injection state shown in FIG. 34, an outer sheath 442 is biased distally by a compressed spring 446. The biasing force of the spring 446 is resisted by the interaction between a corner 452 of the cam 448 and a corner 454 of the outer sheath 442. In this pre-injection configuration, the interaction between the two corners prevents the outer sheath 442 from moving distally under the force of the spring 446. When an injection is delivered, the activating member 444, similar to activating members 416a and 416b shown in FIG. 31, moves distally and contacts the cam 448. This contact causes the cam to rotate to the orientation shown in FIG. 35.

Figure 35:
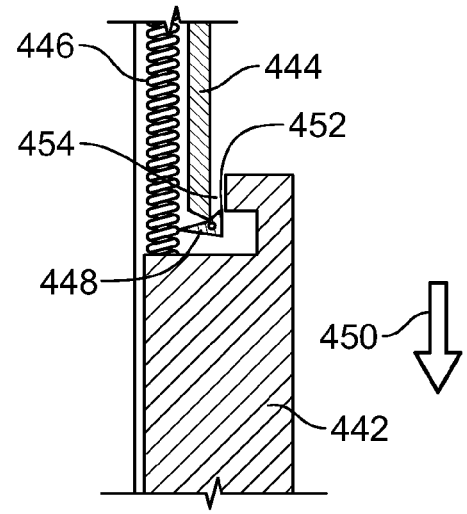
FIG. 35 shows the triggering mechanism shown in FIG. 34 after an injection.

In the post-injection configuration shown in FIG. 35, cam 448 is rotated in a counterclockwise direction relative to the pre-injection configuration. After rotation the corner 452 of the cam 448 is clear of the corner 454 of the outer sheath 442. Thus, the two corners no longer interact to resist the biasing force of spring 446. The outer sheath 442 is free to move distally in the direction of arrow 450 under the force applied by the spring 446. As a result of this distal movement, the outer sheath 442 is able to move and cover a distal needle, similar to the needle 406 shown in FIG. 33.

Figure 36:
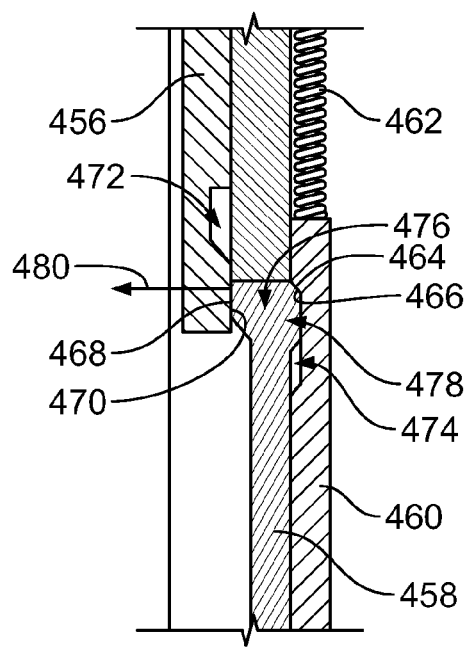
FIG. 36 shows an illustrative triggering mechanism.
Figure 37:
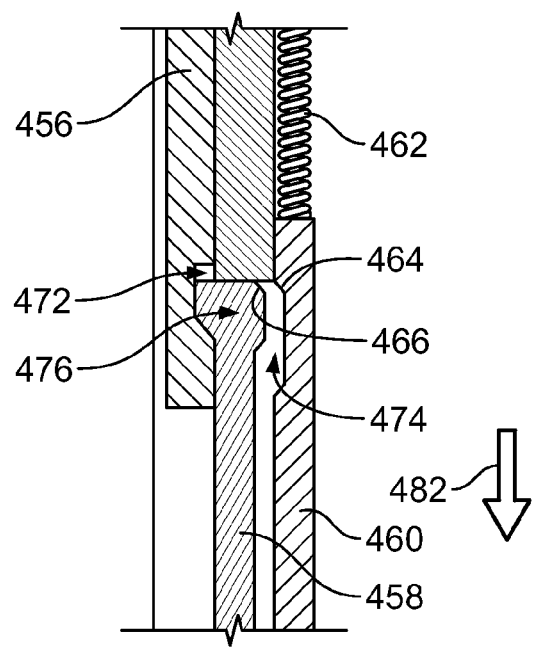
FIG. 37 shows the triggering mechanism shown in FIG. 36 after an injection.

Another embodiment of a forward shielding triggering mechanism is shown in FIGS. 36 and 37. In FIG. 36, an outer sheath 460 is under a biasing force from a compressed spring 462. The distal biasing force is resisted by a head 476 of an inner sheath 458. The head 476 is larger than the width of the rest of the inner sheath 458 and includes a back portion 478 that extends into a pocket 474 of the outer sheath 460. In this position, a surface 466 of the inner sheath contacts a corresponding surface 464 of the outer sheath and prevents the outer sheath from traveling past the head 476, thus resisting the biasing force of the spring 462. The interaction of the two sloped surfaces 464 and 466 pushes the head 476 forward in the direction of arrow 480. Movement in this direction, however, is restricted by the interaction between surface 468 of an activating member 456 and a front surface 470 of the head 476. During an injection, the activating member 456 moves distally, similar to the activating members 416a and 416b, discussed above with respect to FIG. 31. The movement of the activating member 456 aligns the pocket 472 of the activating member in position to receive the head 476. As shown in FIG. 37, once the pocket 472 reaches the head 476, the forward force created by the interaction of surfaces 464 and 466 pushes the head 476 into the pocket 472. In this configuration, the outer sheath 460 is free to move distally in the direction of arrow 482. The spring 462 is able to extend, moving the outer sheath 460 distally and covering a distal needle, as discussed above with respect to FIG. 33.

As described in the above embodiments, a syringe assembly that includes a needle shielding mechanism can provide for safer handling of used needles. A shielding mechanism can trigger automatically when an injection is delivered and shield a needle after injection to protect a user against accidental stabs with a used needle. Additional features may also be provided to enhance the ease of use and convenience of the syringe assembly for a user. One such feature is a bevel orientation mechanism that allows a user to orient a needle bevel prior to delivering an injection using the syringe assembly.

In certain embodiments, a bevel orientation mechanism is included with the syringe assembly 100. As shown in FIGS. 12-16, the bevel orientation collar 108 rotates around the syringe barrel 124 of the syringe to allow the user to adjust the angle at which the bevel of the syringe needle is oriented prior to injection. The interaction between the bevel orientation collar 108 and the syringe barrel 124 may be either direct or indirect, through one or more other intermediate components of the syringe assembly 100. In some embodiments, an inner surface of the bevel orientation collar 108 contacts the syringe barrel 124 and causes it to rotate. In some embodiments, intermediate interactions between internal components of the syringe assembly 100 may translate rotation of the bevel orientation collar 108 into rotation of the syringe barrel 124. For example, a holding component, such as a rubber ring gasket, may be positioned between the bevel orientation collar 108 and the syringe barrel 124. Rotation of the bevel orientation collar 108 would rotate the gasket and syringe barrel 124 held within the syringe assembly 100.

FIGS. 12-16 show an indirect rotational coupling between components of syringe assembly 100 that are configured to provide a bevel orientation mechanism, according to certain embodiments. In the interaction depicted in FIGS. 12-16, the bevel orientation collar 108 does not directly contact or rotate the syringe barrel 124. Rather, the rotation of the bevel orientation collar 108 rotates other internal components of the syringe assembly 100, including the inner sheath 120, the outer sheath 122, and the outer top 128, through internal connections and couplings between the components. The internal components hold a syringe barrel in the syringe assembly, and rotation of these components causes the barrel to rotate. When the syringe barrel is rotated, the needle attached to the barrel can be oriented by a user at any desired angle.

Figure 13:
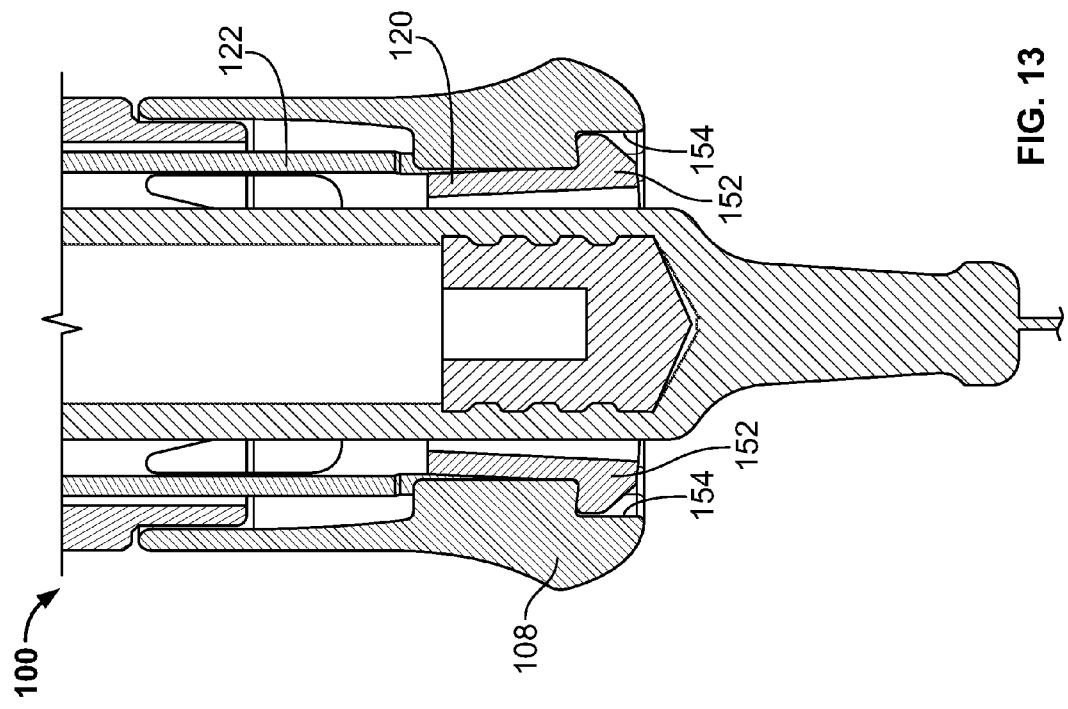
FIG. 13 shows a cross section of bevel orientation components of an illustrative syringe assembly.
Figure 12:
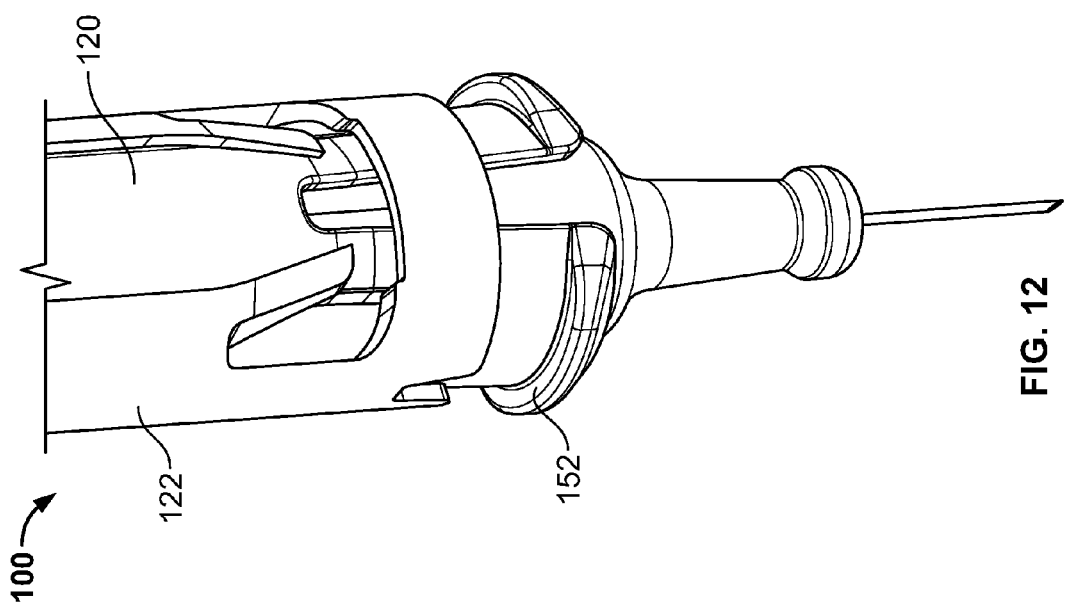
FIG. 12 shows a perspective view of internal bevel orientation components of an illustrative syringe assembly.

FIG. 12 shows the tower end of the syringe assembly 100 with the pull cap 110, bevel orientation collar 108, and housing 104 removed, exposing the inner sheath 120 and outer sheath 122. A portion of the inner sheath 120, including clips 152, is not covered by the outer sheath 122. The dips 152 are configured to snap into notches on the bevel orientation collar of the syringe assembly 100 when the bevel orientation collar is placed onto the syringe assembly 100. FIG. 13 shows a cross-section of the lower end of the syringe assembly 100 with the bevel orientation collar 108 attached. The clips 152 of the inner sheath 120 snap into the notches 154 of the bevel orientation collar 108 and thus couple the inner sheath 120 to the bevel orientation collar 108. As a result of this coupling, the inner sheath 120 rotates whenever a user manually rotates bevel orientation collar 108.

Figure 14:
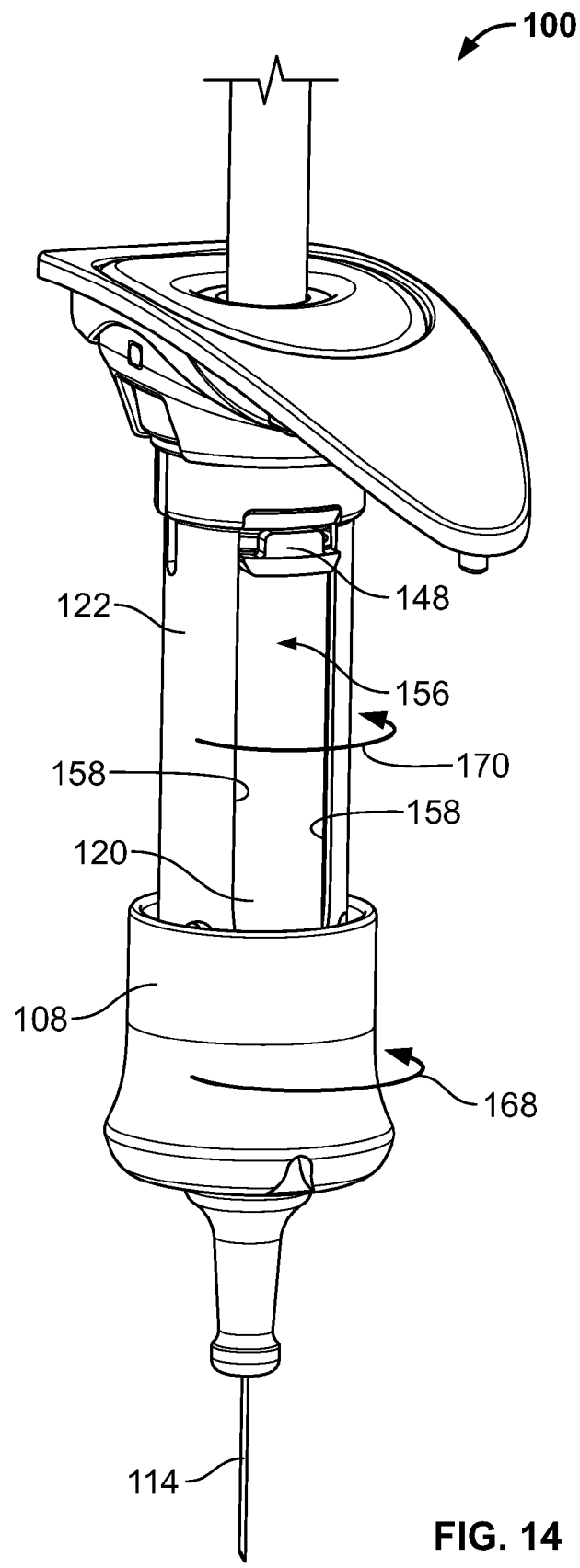
FIG. 14 shows a perspective view of an illustrative syringe assembly.
Figure 15:
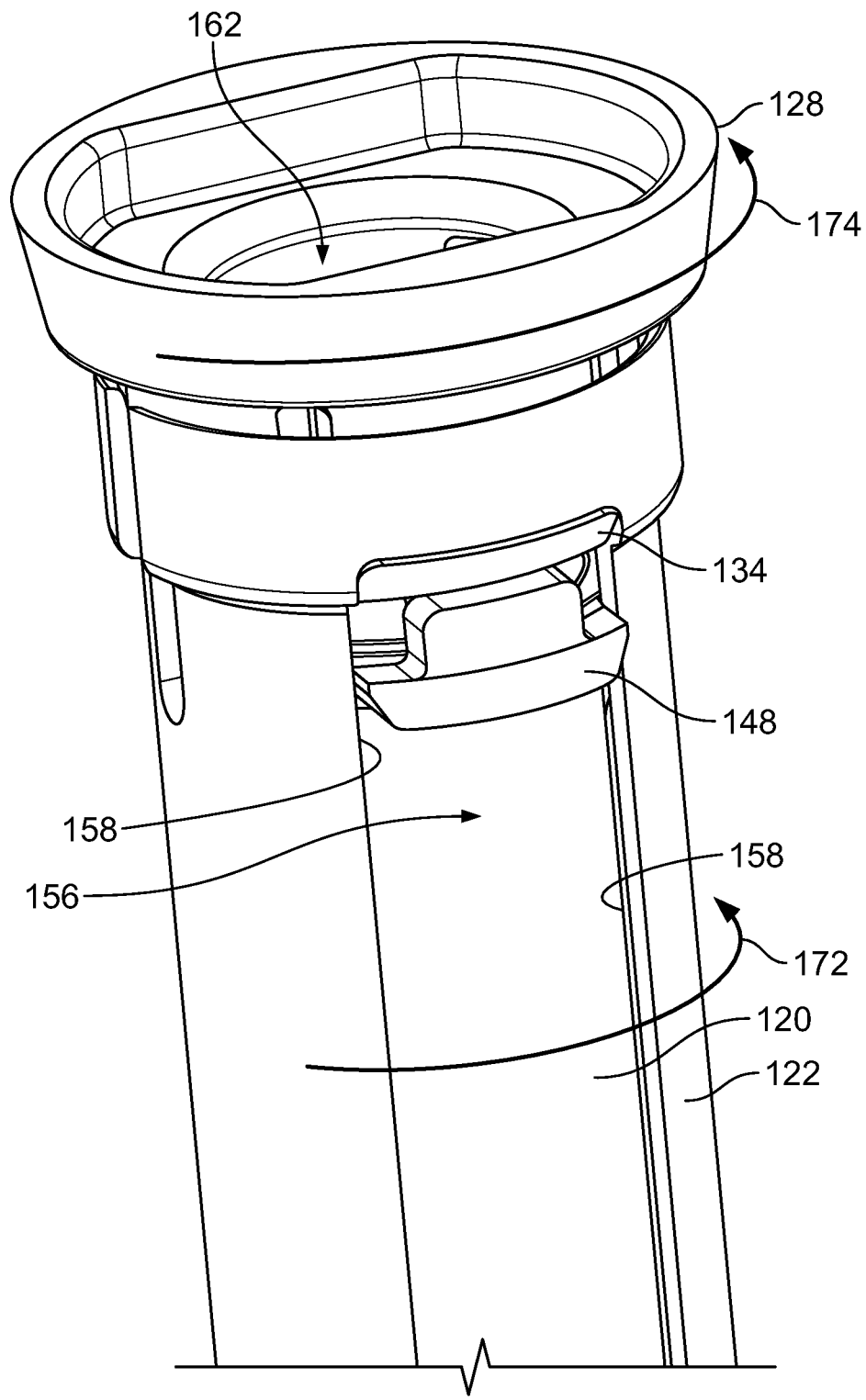
FIGS. 15 and 16 show perspective views of internal components of an illustrative syringe assembly.
Figure 16:
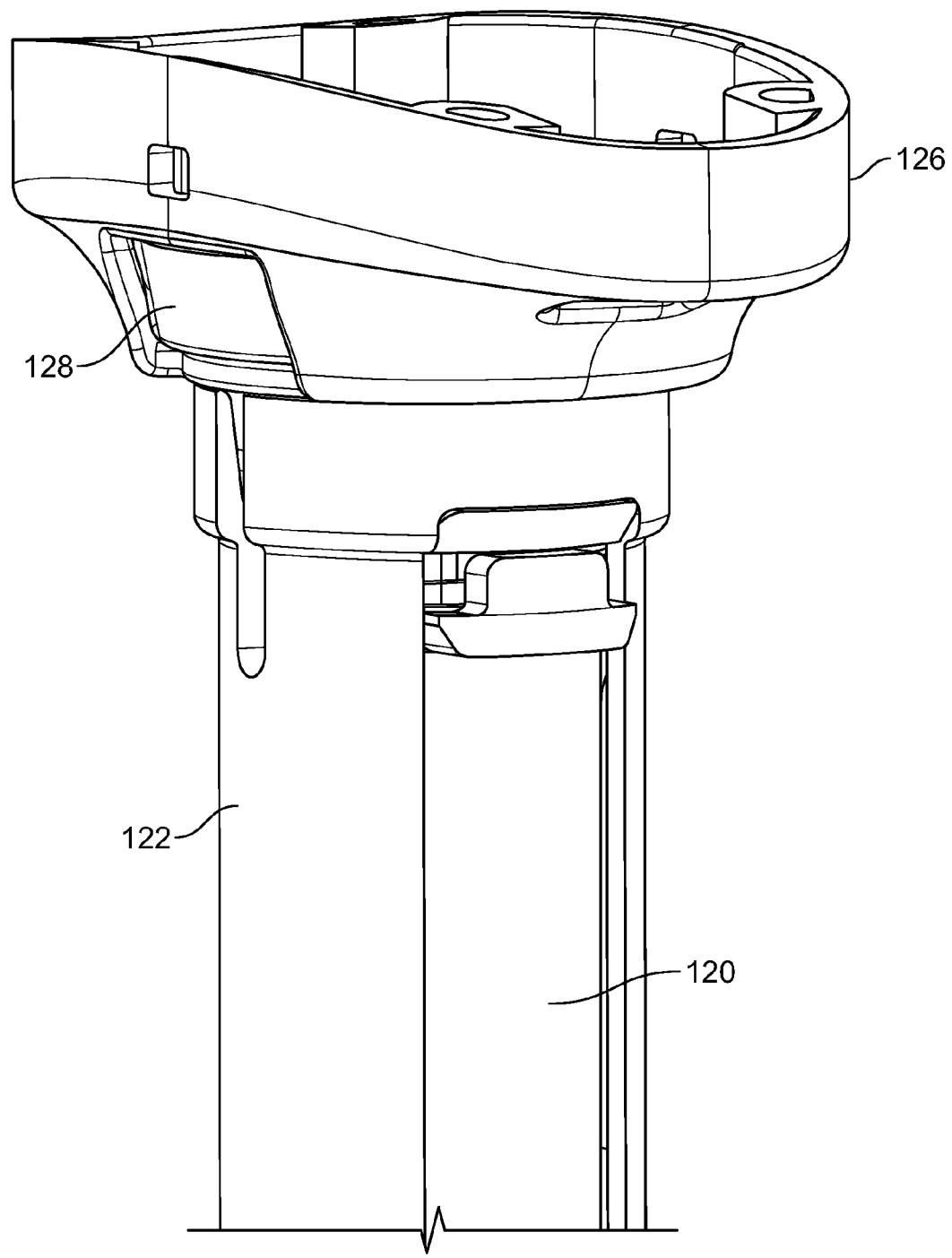

FIGS. 14 and 15 depict One way that rotation of components of the syringe assembly 100 occurs when a user manually rotates the bevel orientation collar 108. As shown, the shelf 148 of the inner sheath 120 extends outward through a slot 156 in the outer sheath 122. The shelf 148 creates a rotational coupling between the inner sheath 120 and the outer sheath 122 by exerting a force on edges 158 of the slot 156 in the outer sheath 122 whenever the inner sheath 120 is rotated. The force exerted on edges 158 by the shelf 148 pushes the outer sheath 122 so it rotates along with the inner sheath 120. Therefore, when the bevel orientation collar 108 is rotated, for example in the direction shown by arrow 168, both the inner sheath 120 and the outer sheath 122 rotate together, for example in the direction shown by arrow 170.

FIGS. 14 and 15 illustrate how rotation of the bevel orientation collar 108 translates into rotation of internal components of the syringe assembly 100 and, ultimately, rotation of the needle 114. When rotation of the bevel orientation collar 108 causes the inner sheath 120 and outer sheath 122 to rotate as shown in FIG. 14, the rotation is also transferred to the outer top 128 as shown in FIG. 15. The clips 134 of the outer top 128 extend outward into the slot 156 in the outer sheath 122 and lock between edges 158 of the slot 156. When the outer sheath 122 rotates, for example in the direction shown by arrow 172, the edges 158 between which clip 134 is locked force the outer top 128 to rotate as well, for example, in the direction shown by arrow 174.

When the syringe assembly 100 is made, the outer top 128 is dropped into the inner housing 126 to hold the outer top 128, inner sheath 120, and outer sheath 122 within the syringe assembly 100 and create the inner chamber that receives the syringe. The inner housing 126 does not rotate within the syringe assembly 100. To allow for unrestrained rotation of the outer top 128, the inner housing 126 has cutouts on either side to accommodate the geometry of the rim of the outer top 128, and allow a portion of the rim of the outer top 128 to extend beyond the sides of the inner housing 126. The accommodating cutouts thus allow the outer top 128 to rotate within the inner housing 126, while the inner housing 126 remains static. In certain embodiments, the inner housing 126 has a different geometry than the outer top 128 that could interfere with rotation of the outer top 128. For example, in the embodiment shown in FIG. 16, the inner housing 126 has a substantially oval shape, while the outer top 128 has a substantially circular shape. Cutouts in the inner housing 126 avoid interference from the sides of the oval-shaped inner housing 126 on the rotation of the circular outer top 128.

The outer top 128 has an opening 162 that receives a collar of a syringe barrel inserted into the syringe assembly 100. The shape of the opening is shaped to match the shape of the syringe barrel collar. As shown in FIG. 15, the shape of this opening and of the syringe barrel collar is preferably non-circular, thus causing a syringe barrel inserted into the syringe assembly 100 to rotate when the outer top 128 rotates as a result of the interaction between the outer top 128 and the collar of the syringe barrel. When the outer top 128 is rotated, the full barrel of the syringe will also rotate, thus causing the needle that extends from the tower end of the syringe assembly 100 to rotate.

During operation of the bevel orientation mechanisms shown herein, rotation of the bevel orientation collar 108 is transferred to rotation of the needle 114, allowing the user to orient and position the needle bevel. To operate the bevel orientation mechanism, a user first manually rotates the bevel orientation collar 108. The notches 154 in the bevel orientation collar 108 hold the clips 152 of the inner sheath 120 and force the clips 152 and inner sheath 120 to rotate along with the bevel orientation collar 108. When inner sheath 120 rotates, the shelf 148 of inner sheath 120 exerts a force on the edges 158 of the slot 156 in the outer sheath 122, which causes the outer sheath 122 to rotate along with the inner sheath 120. The edges 158 of the slot 156 transfer the rotation force of the outer sheath 122 to the outer top 128, which is locked into the slot 156 by clips 134 on the outer top 128. The outer top 128 holds a collar of a syringe barrel in its opening, and the rotation of the outer top 128 causes the barrel 124 of the syringe held within the syringe assembly 100, along with the needle 114 extending from the housing 104 of the syringe assembly 100, to rotate.

FIGS. 17-23 show an illustrative process for making a syringe assembly. Notably, the process shown is a continuous process that allows all components of the syringe assembly to be manufactured at a single manufacturing site. This may be preferable if, for example, special approval or certification is needed for a manufacturing site to be able to place a syringe with medication into the syringe assembly. If such certification is required, the full manufacturing process can be carried out at a single manufacturing site that has such clearance in order to streamline the assembly process.

Figure 17:
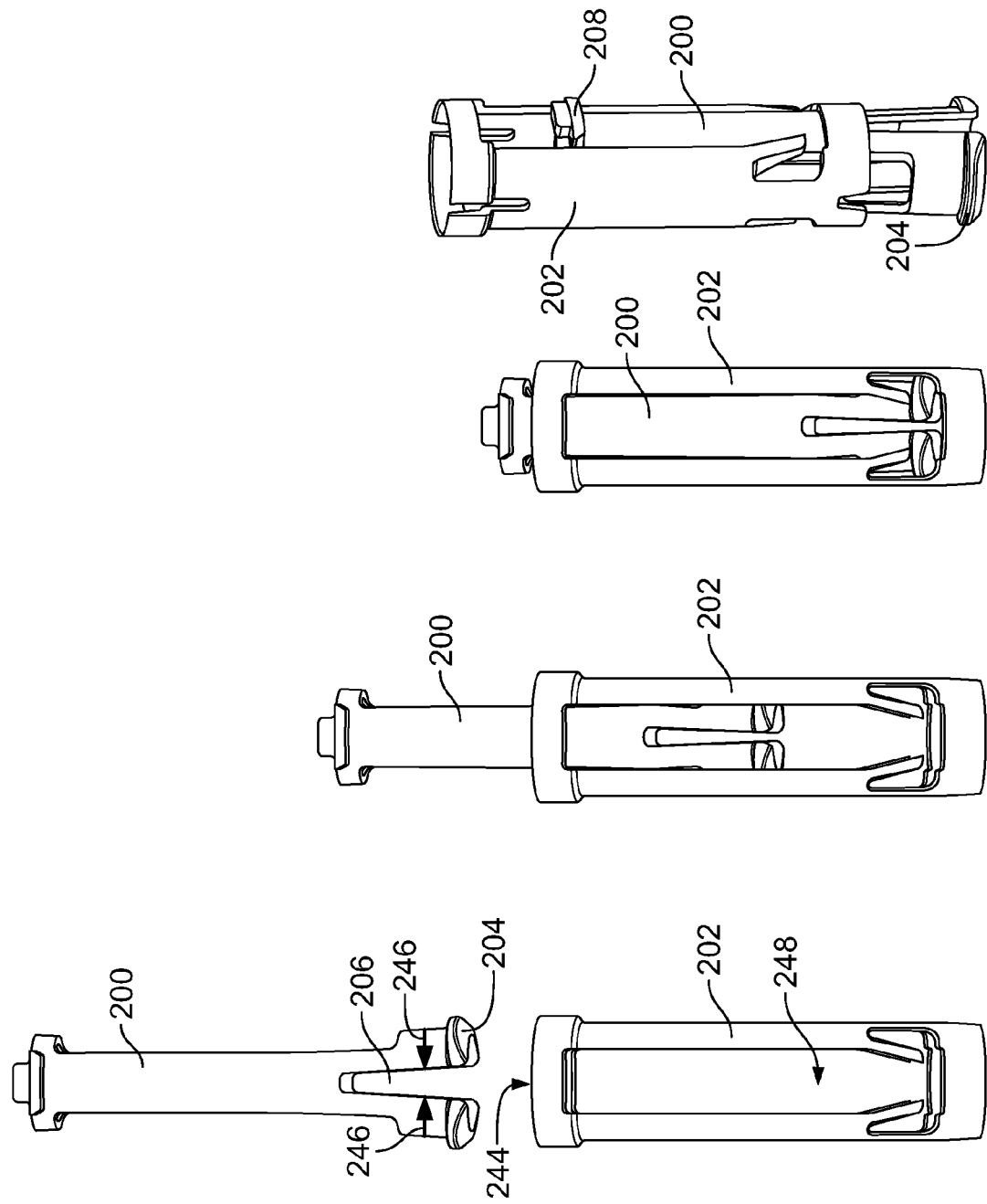

As shown in FIG. 17, the assembly process includes coupling the inner sheath 200 and outer sheath 202. The inner sheath 200 is passed into the top 244 of the outer sheath 202, and clips 204 of the inner sheath 202 contact the outer sheath 202 and deflect inward in the direction shown by arrows 246 due to the slot 206 cut in the inner sheath 200, as the inner sheath 200 passes through the outer sheath 202. These clips 204 then reflect to their original configuration when they pass through the bottom of the outer sheath 202. The inner sheath 200 and outer sheath 202 are aligned such that the shelf 208 of the inner sheath 200 extends laterally outward from the slot 248 in the outer sheath 202 when the two components are assembled together.

Figure 18:
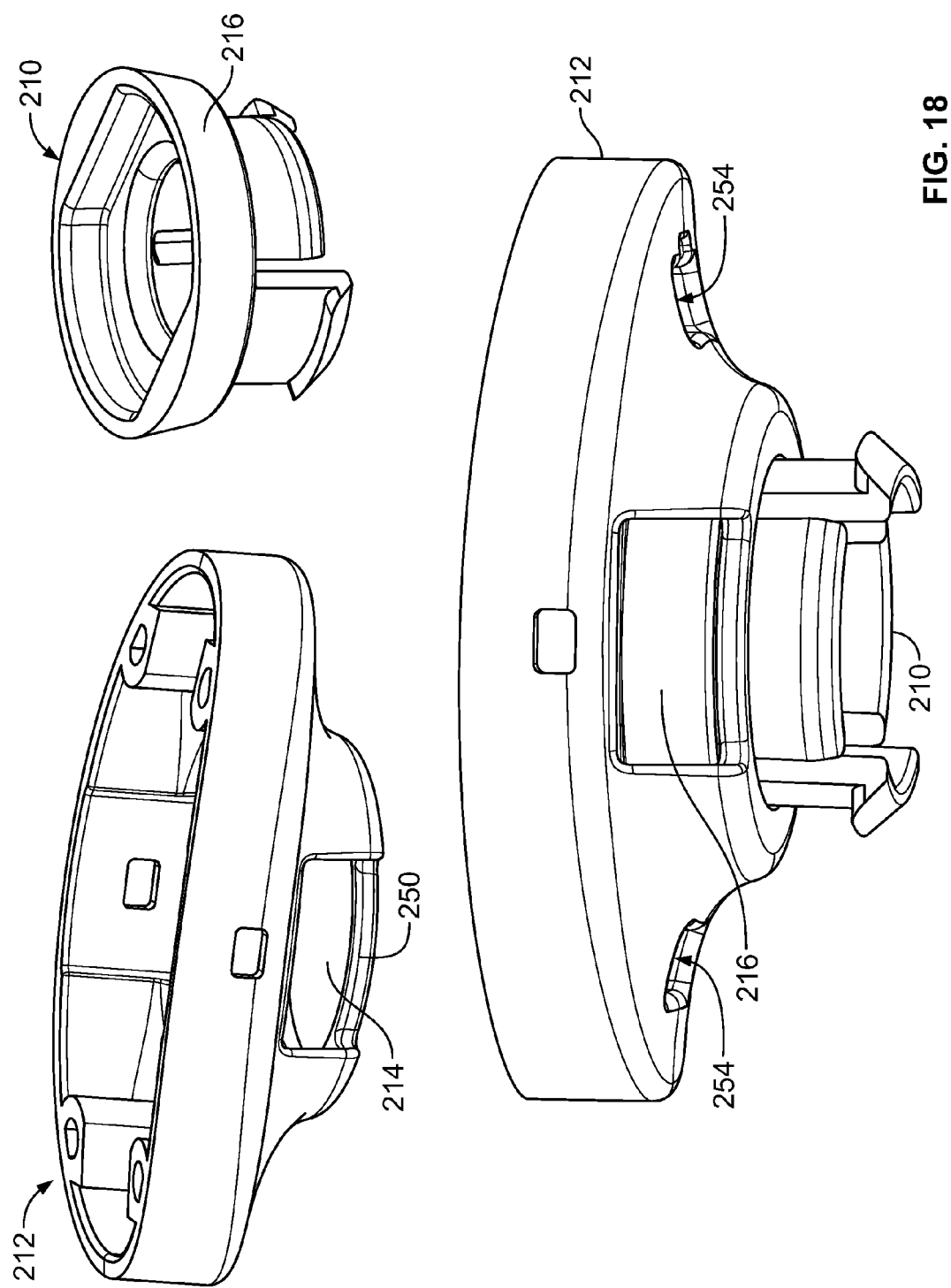

As shown in FIG. 18, the assembly process also includes coupling the outer top 210 and inner housing 212. The outer top 210 is dropped into the top opening of the inner housing 212 and the rim 216 of the outer top 210, which is wider than the bottom edge 250 of the inner housing 212, keeps the outer top 210 from passing through the bottom opening of the inner housing 212. The cutouts 214 on the side of the inner housing 212 receive the rim 216 of the outer top 210. Because the inner housing 212 and outer top 210 have different geometries, the cutouts 218 allow the rim 216 to extend beyond the sides of the inner housing 212. This allows the outer top 210 to rotate independently of the inner housing 212, as the sides of the inner housing 210 do not inhibit the rotation of the outer top 210.

Figure 19:
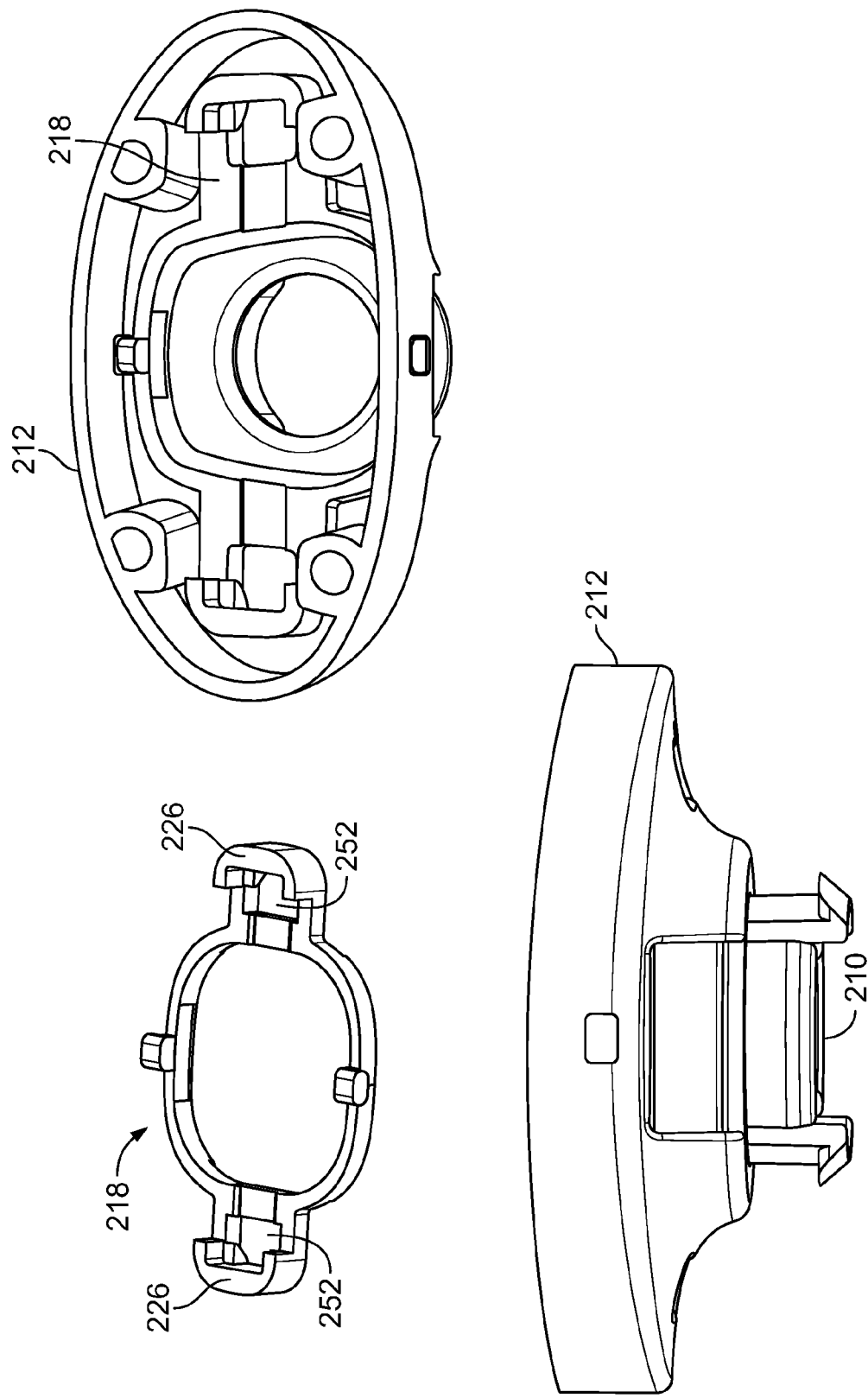

A retainer 218 is placed into the assembly of the inner housing 212 and outer top 210, as shown in FIG. 19. Once the retainer 218 is dropped into the assembly, openings 252 on the lateral ends 226 of the retainer 218 align with corresponding openings 254 in the inner housing 212 to create spaces that will later receive the retaining clips 224 of a housing 220. The retainer 218 shown in FIG. 19 is not configured to contact an injection plunger in the finished syringe assembly, and thus requires an actuator that triggers the shield mechanism to be subsequently added to the assembly later. In certain embodiments, a retainer that includes a collar or some other mechanism for contacting a syringe plunger and does not require an intermediate actuator may be added at this step instead of retainer 218.

Figure 20:
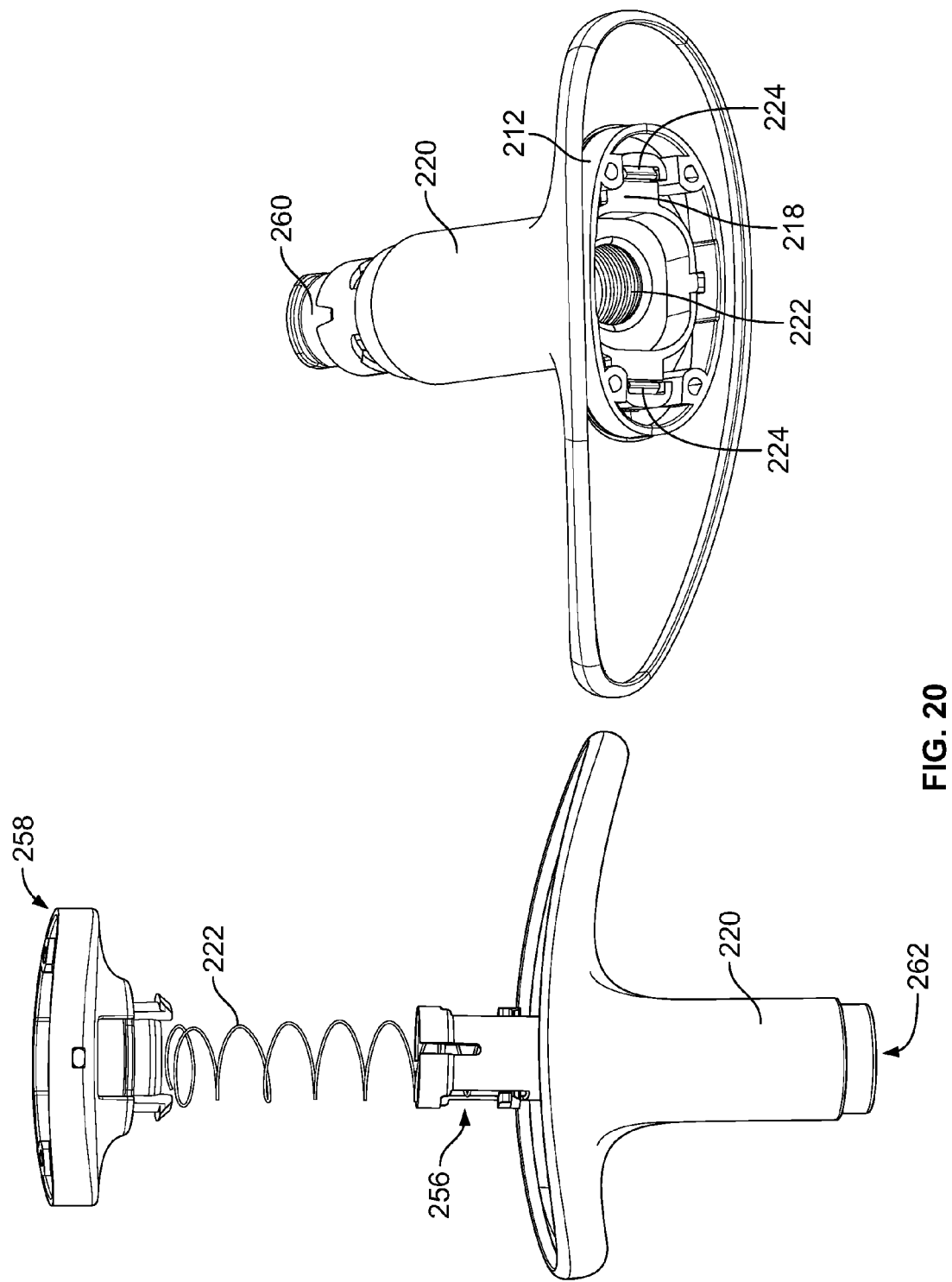

As shown in FIG. 20, the sheath assembly 256, the inner housing assembly 258, and a housing 220 are coupled with a spring 222 to create the spring-loaded needle shielding mechanism of the syringe assembly. To assemble the components, the assembly 256 of the inner sheath 200 and outer sheath 202 is placed into the housing 220, and the lower end 260 of the inner sheath 200 extends beyond the lower opening 262 of the housing 220. The spring 222 is placed within the outer sheath 202 and rests on the upper end of the inner sheath 200. The assembly attic retainer 218, inner housing 212 and outer top 210 is then placed on the top end of the spring 222 such that the spring 222 contacts a portion of the outer top 210. The outer top 210 and inner housing 212 assembly 258 is then pressed downward toward the sheath assembly, compressing the spring 222 and spring-loading the shielding-firing mechanism. The spring-loaded mechanism is locked in place after the retainer 218, inner housing 212 and outer top 210 are pressed into the housing 220 and the retaining clips 224 on the housing 220 engage the lateral ends 226 of the retainer 218.

As shown in FIG. 21, a bevel orientation collar 228 is placed onto the lower end of the syringe assembly. Once the components of the needle shielding mechanism are locked in place, the bevel orientation collar 228 is placed over the outer and inner sheath 200 and contacts the housing 220. The clips 204 of the inner sheath 200 engage the notches 230 on the bevel orientation collar 228 to couple the two components, as discussed above with respect to FIGS. 12 and 13. At this point in the assembly process, the needle-shielding mechanism is spring-loaded, and the bevel orientation collar 228 is rotated so as to rotate the inner sheath 200 and outer sheath 202, which in turn causes rotation of the outer top 210. With the bevel orientation mechanism and shielding mechanism assembled, the syringe assembly is ready to receive a syringe.

Figure 22:
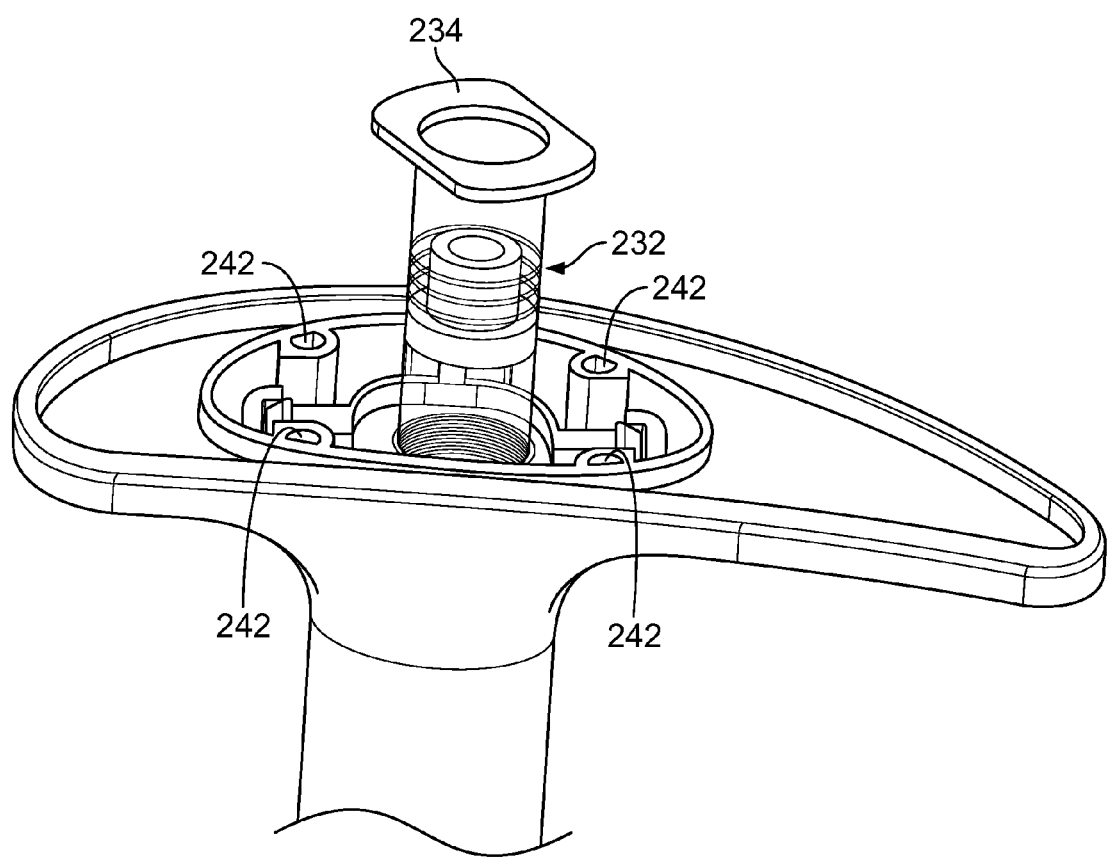

A syringe 232 is placed into the assembly as shown in FIG. 22. The syringe may be pre-filled with a certain dosage of medication, or may be an empty standard hypodermic syringe that can be filled with medication by a user prior to injection. As shown, the top collar 234 of the syringe 232 is a non-circular shape that matches the shaped opening of the outer top 210. The non-circular shape of the top collar 234 and the opening of the outer top 210 rotatably couples the two components.

Figure 23:
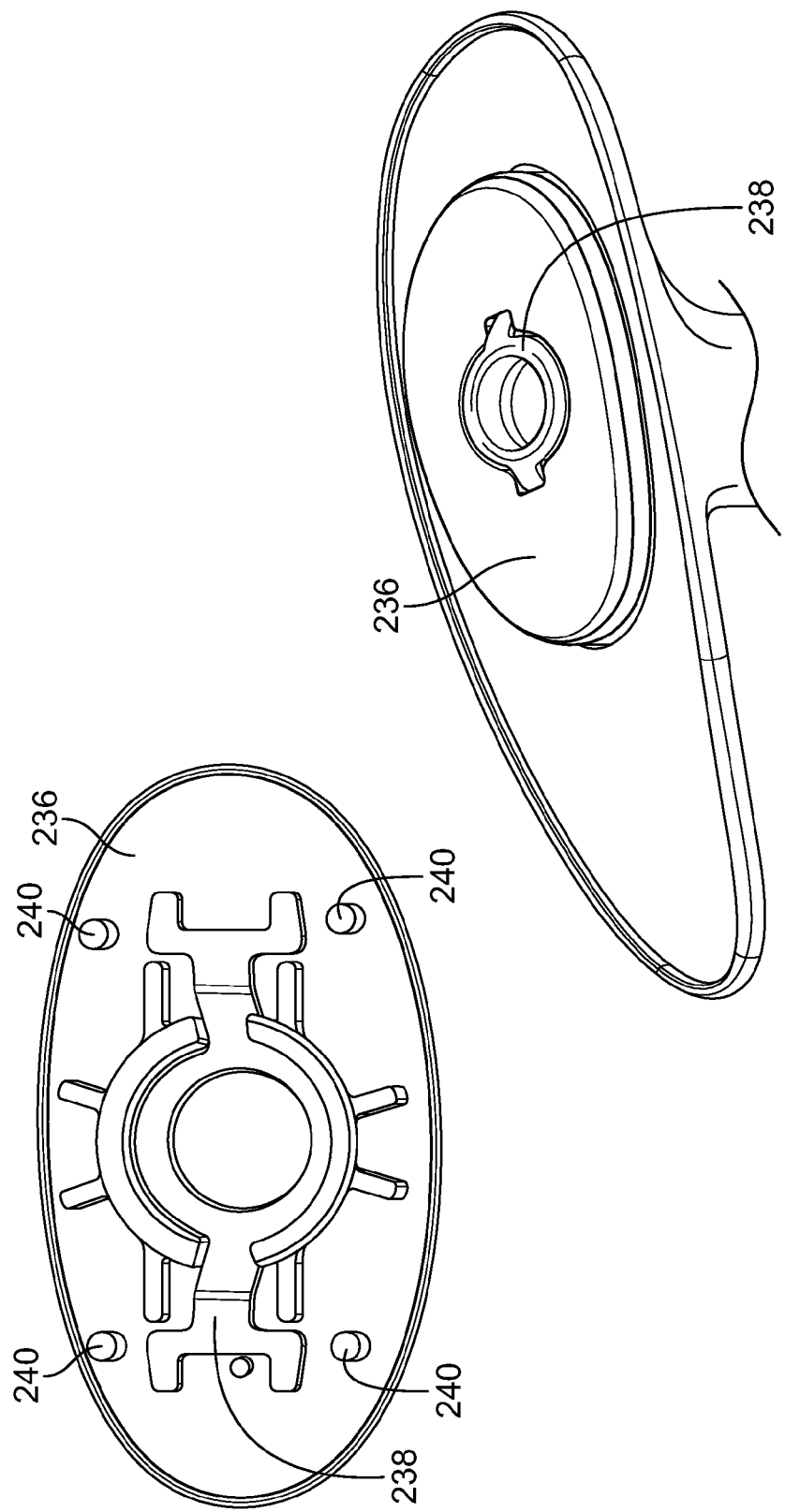

The top cover 236 and an actuator 238 are placed onto the assembly as shown in FIG. 23. The actuator 238 is configured to interact with retainer 218 in the finished assembly. The actuator 238 is positioned and shaped such that a force will be exerted on the actuator 238 by a plunger when an injection is given, and the force will be transferred to the retainer 218 to trigger the needle shielding mechanism. In certain embodiments, a retainer may be used that interacts with a plunger directly, and only a top cover without any actuator is placed on the assembly in this step. The round pegs 240 on the underside of the top cover 236 are placed into the receiving holes 242 in the inner housing 212 shown in FIG. 22. When the top cover 236 and actuator 238 are placed onto the assembly, the ends 226 of the actuator 238 contact the retainer 218. This contact creates the mechanism that moves the retainer 218 laterally and triggers the needle shielding mechanism when a plunger is depressed into the syringe assembly. Finally, to complete the assembly, a plunger is placed into the syringe assembly and a pull cap is placed over the needle.

It is to be understood that the foregoing description is merely illustrative and is not to be limited to the details given herein. While several embodiments have been provided in the present disclosure, it should be understood that the disclosed systems, devices, and methods, and their components, may be embodied in many other specific forms without departing from the scope of the disclosure.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:
1. A syringe assembly including a bevel orientation mechanism, said assembly comprising:
    a housing having an inner chamber with a first opening for receiving a syringe and a second opening to allow a needle of the syringe to extend beyond the housing;
    a collar coupled to the second opening of the housing; and a first sheath disposed within the collar and the housing, wherein rotation of the collar relative to the housing drives rotation of a syringe inserted into the syringe assembly.

2. The syringe assembly of claim 1, wherein the collar has a 360 degree range of rotational motion within the housing.

3. The syringe assembly of claim 1, wherein the collar directly contacts the syringe and causes the syringe to rotate when the collar is rotated.

4. The syringe assembly of claim 1, further comprising a holding component positioned within the collar and operatively coupling the collar to a syringe inserted into the syringe assembly.

5. The syringe assembly of claim 1, wherein the collar is an independent component that can be separated from the housing.

6. The syringe assembly of claim 1, wherein the first sheath is operatively coupled to the collar.

7. The syringe assembly of claim 6, wherein the first sheath includes clips that are configured to mate with notches on the collar to couple the first sheath and the collar.

8. The syringe assembly of claim 7, wherein the clips are releasable and allow the first sheath to move along a longitudinal axis of the inner chamber when released.

9. The syringe assembly of claim 6, further comprising a second sheath operatively coupled to the first sheath.

10. The syringe assembly of claim 9, wherein the second sheath is configured to receive a syringe inserted into the syringe assembly.

11. The syringe assembly of claim 9, further comprising an outer top coupled to the second sheath.

12. The syringe assembly of claim 11, wherein an opening of the outer top is shaped to match a shape of a collar of an inserted syringe.

13. The syringe assembly of claim 12, wherein the opening of the outer top is a non-circular shape.

14. The syringe assembly of claim 11, further comprising an inner housing at the first opening of the housing, wherein the second sheath is held within the housing by the inner housing.

15. The syringe assembly of claim 14, wherein the inner housing does not rotate relative to the housing but allows the second sheath and outer top to rotate relative to the housing.

16. The syringe assembly of claim 14, wherein the inner housing includes at least one cutout that holds the outer top and allows rotation of the outer top while the inner housing remains static.

17. The syringe assembly of claim 9, wherein rotation of the collar causes rotation of the first sheath, second sheath, and a syringe inserted into the syringe assembly relative to the housing.

18. The syringe assembly of claim 1, wherein the collar is configured to be releasably coupled to a pull cap that covers a needle of the syringe assembly.

* * * * *